United States Patent [19]

Lau et al.

[11] Patent Number: 5,589,467
[45] Date of Patent: Dec. 31, 1996

[54] 2,5',N6-TRISUBSTITUTED ADENOSINE DERIVATIVES

[75] Inventors: Jesper Lau, Farum; Lars J. S. Knutsen, Vedbæk, both of Denmark

[73] Assignee: Novo Nordisk A/S, Bagsvaerd, Denmark

[21] Appl. No.: 306,232

[22] Filed: Sep. 14, 1994

[30] Foreign Application Priority Data

Sep. 17, 1993 [DK] Denmark .................................. 1043/93
Mar. 16, 1994 [DK] Denmark .................................. 0310/94

[51] Int. Cl.⁶ .......................... A61K 31/70; C07H 19/67
[52] U.S. Cl. ........................................... 514/46; 536/27.6
[58] Field of Search ............................. 536/27.6; 514/46

[56] References Cited

U.S. PATENT DOCUMENTS

| | | | |
|---|---|---|---|
| 3,819,613 | 6/1974 | Marunoto et al. | 260/211.5 |
| 3,910,885 | 10/1975 | Moffatt et al. | 260/211.5 |
| 4,962,194 | 10/1990 | Bridges | 536/26 |
| 5,308,837 | 5/1994 | Bowlin | 514/46 |

FOREIGN PATENT DOCUMENTS

| | | |
|---|---|---|
| 0181128B1 | 10/1985 | European Pat. Off. . |
| 0253962B1 | 4/1987 | European Pat. Off. . |
| 0232813A2 | 8/1987 | European Pat. Off. . |
| 0181129B1 | 3/1989 | European Pat. Off. . |
| WO90/05526 | 5/1990 | European Pat. Off. . |
| 0402752A2 | 12/1990 | European Pat. Off. . |
| 0423777A2 | 4/1991 | European Pat. Off. . |
| WO91/04032 | 4/1991 | European Pat. Off. . |
| 0490818A1 | 12/1991 | European Pat. Off. . |
| 1101108 | 11/1968 | United Kingdom . |
| 131501 | 5/1974 | United Kingdom . |
| 0152944A2 | 2/1985 | WIPO . |
| WO88/03147 | 5/1988 | WIPO . |
| WO92/02214 | 2/1992 | WIPO . |
| WO93/08206 | 4/1993 | WIPO . |
| WO93/23417 | 11/1993 | WIPO . |
| WO93/23418 | 11/1993 | WIPO . |
| WO94/02497 | 2/1994 | WIPO . |
| WO94/06438 | 3/1994 | WIPO . |

OTHER PUBLICATIONS

Noir et al. Tetrahedron Letters 49(11):2169–2184, 1993.
Klotz et al. Chemical Abstract, vol. 112, Abstr. No. 115221w, Naunyn–Schmiedeberg's Arch. Pharmacol. 340161:679–83, 1989.

Primary Examiner—Gary L. Kunz
Attorney, Agent, or Firm—Steve T. Zelson, Esq.; Elias J. Lambiris, Esq.

[57] ABSTRACT

A compound of formula (I), or a pharmaceutically acceptable salt thereof:

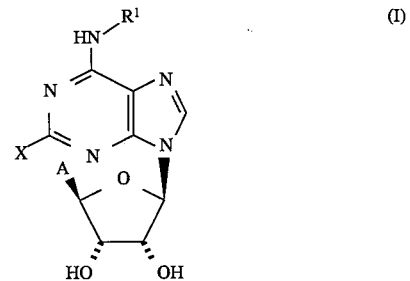

(I)

wherein

X is halogen, amino, perhalomethyl, cyano, $C_{1-6}$-alkoxy, $C_{1-6}$-alkylthio or $C_{1-6}$-alkylamino;

A is methyl, halomethyl, cyanomethyl, aminomethyl, vinyl, methylthiomethyl or methoxymethyl;

$R^1$ is selected from optionally substituted N-bonded heterocyclics.

The compounds have been found useful for treating central nervous system ailments.

14 Claims, No Drawings

2,5',N6-TRISUBSTITUTED ADENOSINE DERIVATIVES

The present invention relates to therapeutically active N-substituted 5'-deoxy adenosine derivatives further substituted at the 2- and 5' positions and pharmaceutically acceptable addition salts thereof, and their pharmaceutical compositions as well as methods for using the compounds and compositions described.

BACKGROUND OF THE INVENTION

Adenosine is a naturally occurring purine nucleoside, from which is derived a range of agonists at adenosine receptors having considerable potential in the treatment of human disease (Life Sciences, 1991, 49, 1435–1453; Journal of Medicinal Chemistry, 1992, 35, 407–422; Annual Reports in Medicinal Chemistry, 1993, 28, 295–304).

Adenosine has been shown to have a number of significant effects on the mammalian central nervous system (CNS) (Annual Reports in Medicinal Chemistry, 1988, 23, 39–48; Adenosine in the Nervous System, T. W. Stone, Ed., Academic Press Ltd., London 1991) especially under conditions of neuronal stress where the compound appears to act as an endogenous neuroprotectant (Progress in Neurobiology, 1988, 31, 85–108, Trends in Pharmacological Sciences, 1992, 11, 439–445). For example, the concentration of adenosine has been demonstrated to rise greatly in certain brain regions following epileptic seizures or conditions of neuronal ischaemia/anoxia (Brain Research, 1990, 516, 248–256).

It has been established for some years now that centrally acting adenosine receptor agonists or compounds which increase extracellular adenosine levels can exhibit what is termed neuromodulator activity (Trends in Neurosciences, 1984, 164–168). Such substances influence (Trends in Neurosciences, 1984, 164–168). Such substances influence the release of neurotransmitters in regions of the central nervous system (Annual Review of Neuroscience, 1985, 8, 103–124; Trends in Neurosciences, 1984, 164–168), with particular inhibitory effects on the release of the excitatory amino acid glutamic acid (glutamate) in the CNS (Nature, 1985, 316, 148–150) especially under ischaemic conditions (Journal of Neurochemistry, 1992, 58, 1683–1690).

There are several CNS ailments for which this adenosine receptor mediated neuromodulator activity is accepted by persons skilled in the art as being of clear therapeutic benefit including the treatment of convulsive disorders (European Journal of Pharmacology, 1991, 195, 261–265; Journal of Pharmacology and Experimental Therapeutics, 1982, 220, 70–76; European Journal of Pharmacology, 1993, 242, 221–228), prevention of neurodegeneration under conditions of brain anoxia/ischaemia (Neuroscience Letters, 1987, 83, 287–293; Stroke, 1988, 19, 1133–1139; Neuroscience, 1989, 30, 451–462; Pharmacology of Cerebral Ischaemia 1990, (Kriegelstein, J. and Oberpichler, H., Eds., Wissenschaftliche Verlagsgesellschaft mbH: Stuttgart, 1990, pp 439–448; Trends in Pharmacological Sciences 1992, 11, 439–445) or the use of a purinergic agent in the treatment of pain (European Journal of Pharmacology, 1989, 162, 365–369; Neuroscience Letters, 1991, 121, 267–270).

Adenosine receptors represent a subclass ($P_1$) of the group of purine nucleotide and nucleoside receptors known as purinoreceptors. This sub-class has been further classified into distinct receptor types which have become known as $A_1$, $A_2$ and $A_3$. Extensive research has been carried out in a quest to identify selective ligands at these sites. Selective ligands exist for $A_1$, $A_2$ and $A_3$ adenosine receptors and the structure-activity relationships of the various reference ligands have been reviewed (Comprehensive Medicinal Chemistry, Volume 3, (Hansch, C., Sammes, P. G. and Taylor, J. B., Eds., Pergamon Press PLC: 1990, pp 601–642, Journal of Medicinal Chemistry, 1994, 37, 636–646). Among the known adenosine receptor agonists most selective for the $A_1$ receptor over the $A_2$ receptor are the examples where the adenine nucleus is substituted with a cycloalkyl group on the amino function, for example N-cyclopentyladenosine (CPA) and N-cyclohexyladenosine (CHA) (Journal of Medicinal Chemistry, 1985, 28, 1383–1384) or 2-chloro-N-cyclopentyladenosine (CCPA) (Naunyn-Schmiedeberg's Arch. Pharmacol. 1988, 337, 687–689).

There is evidence for further subdivision of adenosine receptors into the subtypes $A_{2a}$, $A_{2b}$ (of high and low affinity) $A_3$ and $A_4$. The latest status of these subtypes has been reviewed (Drug Development Research, 1993, 28, 207–213; Trends in Pharmacological Sciences 1993, 290–291; Pharmacological Reviews, 1994, 46, 143–156). The $A_3$ receptor (Proceedings of the National Academy of Sciences of the USA, 1992, 89, 7432–7436; Trends in Pharmacological Sciences, 1994, 15, 298–306) appears to be responsible for some of the cardiovascular effects of reference ligands (British Journal of Pharmacology, 1993, 109, 3–5).

Various examples of N-heteroarylalkyl substituted $A_1$ selective adenosine analogues have been reported in the literature. It should be noted that some of these are named as $N^6$-substituted adenosine derivatives, but this is equivalent to ACS-approved nomenclature where compounds substituted on adenosine's 6-amino position are referred to as N-substituted adenosine derivatives. Derivatives of adenosine with the heteroatoms sulphur, oxygen or nitrogen bonded directly to the 6-amino substituent are not common in the chemical literature, but those cases known are summarised below.

Derivatives with hydrogen at the purine 2-position include N-aminoadenosine, N-[(N-methyl-N-phenyl)amino]adenosine, N-hydroxyadenosine, N-methoxyadenosine and N-benzyloxyadenosine (Journal of Medicinal Chemistry, 1985, 28, 1636–1643); N-ethoxyadenosine (Chemical and Pharmaceutical Bulletin, 1973, 21, 1676–1682; ibid., 1973, 21, 1835–1838); N-(methylamino) adenosine and N-[(N-hydroxy-N-methyl)amino]adenosine (Journal of Medicinal Chemistry, 1968, 11, 521–523). A range of compounds which have no further substitution on the ribose moiety have been published by Novo Nordisk (Bioorganic and Medicinal Chemistry Letters, 1993, 3, 2661–2666).

Examples of adenosine derivatives with oxygen or nitrogen atoms bonded to the 6-amino substituent, containing an additional purine 2-substituent are 2-amino-N-hydroxyadenosine (Journal of Medicinal Chemistry, 1972, 15, 387–390); 2-amino-N-aminoadenosine (Chemical and Pharmaceutical Bulletin, 1969, 17, 2373–2376); 2-amino-N-methoxyadenosine (Chemical and Pharmaceutical Bulletin, 1975, 23, 464–466); 2-chloro-N-hydroxyadenosine (Journal of Medicinal Chemistry, 1991, 34, 2226–2230), 2-fluoro-N-hydroxyadenosine and 2-fluoro-N-aminoadenosine (Journal of Medicinal Chemistry, 1970, 13, 427–430) and 2-fluoro-N-methoxyadenosine (Journal of Medicinal Chemistry, 1971, 14, 816–819). These articles involve compounds with intact ribose moieties.

In the above scientific articles, no mention is made of any pharmacological effects of the compounds concerned on the central nervous system.

There are also very few examples of compounds designed as adenosine receptor agonists where the ribose moiety in adenosine is chemically modified, and many of those known have poor affinity for the adenosine receptor (Journal of Medicinal Chemistry, 1986, 29, 346–353). However, minor modifications at the 3'- and 5'-positions appear to be allowed and amongst these the 5'-chloro-5'-deoxy adenosines show particularly good receptor affinity (Journal of Medicinal Chemistry, 1989, 32, 8–11). Other scientific articles also describe 5'-modifications of adenosine derivatives (Journal of Medicinal Chemistry, 1986, 29, 1683–1689).

EP Publications No. 181,128 and 181,129 disclose 5'-deoxy adenosine derivatives containing 5'-hydrogen, 5'-halogen and 5'-methylthio, which are claimed to have desirable antiinflammatory, analgesic as well as CNS and antihypertensive properties respectively. EP Publication No. 232,813 discloses N-substituted adenosines including a larger range of 5'-modified compounds which are also claimed to have desirable CNS and antihypertensive properties. PCT Publication WO 94/02497 reveals certain sulphohydrocarbon derivatives of adenosine, where the possibility exists for substitution at the 5'-position of the ribose moiety. In PCT Publication WO 88/03147 5'-substituted adenosine derivatives with selectivity for the adenosine A2 receptor are disclosed.

In U.S. Pat. No. 4,962,194 methods for preparing 5', N-disubstituted adenosine derivatives are revealed. GB Patent No. 1,101,108 discloses 5', N-disubstituted adenosine analogues which possess cardiovascular activity. U.S. Pat. No. 3,910,885 reveals 4'-alkoxy and 4'-haloalkoxy nucleosides. PCT Publication WO 94/06348 discloses a number of pyrrolo[3,4-d]pyrimidine structures which are formally isosteric with adenosine and which are modified with substituents at the sugar 5'-position. U.S. Pat. No. 5308837 covers the use of 5'-amine substituted adenosine analogues as immunosuppressants.

In U.S. Pat. No. 3,819,613, substituted adenosine analogues with hydrazone derivatives on the 6-amino function are disclosed as hypotensive agents. In GB Patent No. 1,351,501, adenosine and 2-aminoadenosine derivatives having a —NH—$R_2$ group joined to the 6-amino function are disclosed as coronary dilators and platelet aggregation inhibitors. In EP Publication No. 152,944, a series of 2-, 6- and 8-substituted adenosine derivatives are described having activity as antiallergy agents. In EP Publication No. 253,962, adenosine and 2-haloadenosine analogues having an alkyl, cycloalkyl or an aralkyl group attached to the 6-amino function are described with activity as antidementia agents.

In EP Publication No. 402,752, derivatives of adenosine unsubstituted in the 2-position are described which have a substituted heteroaromatic 1-pyrrolyl moiety attached to the 6-amino group. In PCT Publication No. WO 91/04032, methods of preventing neural tissue damage in neurodegenerative diseases by increasing extracellular concentrations of adenosine are described. Examples are given of prodrug esters of AICA riboside which are claimed to be centrally acting neuroprotective agents. In PCT Publication No. WO 92/02214, analogues of AICA riboside are described which increase extracellular adenosine levels with beneficial effects claimed in peripheral and CNS ischaemia. In PCT Publication No. WO 90/05526, 2-(alkylalkynyl)adenosine derivatives are described for treatment of ischaemic disease of the heart and brain. In EP Publication No. 423 777 a method for treating gastrointestinal motility disorders using N(6) (substituted aminoalkyl) adenosine derivatives is disclosed. EP Publication No. 490 818 describes a new use of 2'-O-methyl adenosine derivatives for a range of ailments including neurodegenerative disorders.

The present invention relates to new adenosine analogues with modified ribose moieties which show potent binding in vitro to the adenosine A1 receptor, and which also display selectivity for $A_1$ receptor binding in vitro over that to the $A_2$ receptor subtype. In addition, the compounds contained in this invention have a relatively high lipophilicity, especially when compared to adenosine analogues which are not substituted on the 6-amino group or the purine 2-position. This latter property makes these compounds suitable for passage across the blood brain barrier.

The compounds are also substrates for nucleoside-specific active transport systems into the CNS across the blood barrier. These useful properties support the notion that the compounds are candidate drugs for treatment of the CNS ailments mentioned within this invention in humans as well as cardiovascular disorders such as cardiac ischaemia.

The compounds of the invention are purine derivatives of formula I, or a pharmaceutically acceptable salt thereof:

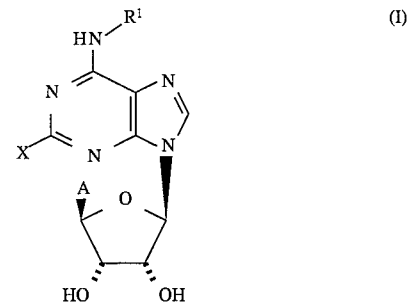

wherein

X is halogen, amino, perhalomethyl, cyano, $C_{1-6}$-alkoxy, $C_{1-6}$-alkylthio or $C_{1-6}$-alkylamino;

A is methyl, halomethyl, cyanomethyl, aminomethyl, vinyl, methylthiomethyl or methoxymethyl;

$R^1$ is selected from the groups consisting of

wherein Q is nitrogen or carbon, n is 1 to 3 and where the group (a) may be optionally substituted with one or two $C_{1-6}$-alkyl groups, $C_{2-6}$-alkenyl, $C_{2-6}$-alkynyl, phenoxy, phenylsulphonyl, phenylsulphinyl, phenylthio, hydroxy, phenyl, $C_{1-6}$-alkoxy or $C_{1-6}$-alkoxy-$C_{1-6}$-alkyl, phenylthioalkyl or

wherein Y is O, S or NZ, where Z is H, $C_{1-6}$-alkyl or phenyl, and where the group (b) may be optionally substituted with $C_{1-6}$-alkyl, $C_{2-6}$-alkenyl, $C_{2-6}$-alkynyl, phenoxy, phenyl, $C_{1-6}$-alkoxy or $C_{1-6}$-alkoxy-$C_{1-6}$-alkyl, or $R^1$ is —$NR^2R^3$ or —$YR^4$, wherein Y is oxygen;

$R^2$ is $C_{1-6}$-alkyl;

$R^3$ is phenyl or $C_{1-6}$-alkyl which may be substituted by phenyl or phenoxy;

$R^4$ is $C_{1-6}$-alkyl or $C_{3-8}$-cycloalkyl, which may be substituted by phenyl or phenoxy.

In certain examples, the group $R^1$ can contain one or more asymmetric carbon atoms in addition to those asymmetric centres already present in the molecule. In examples where this is the case, this invention includes all resulting diastereoisomers and mixtures thereof.

Various salts of compounds of formula (I) can be prepared which is physiologically acceptable. These include addition salts derived from inorganic or organic acids, for example, acetates, fumarates, glutarates, glutaconates, lactates, maleates, methanesulphonates, phosphates, salicylates, succinates, sulphates, sulphamates, tartrates and paratoluenesulphonates. In some cases, solvates of either the free nucleosides or the acid addition salts can be isolated and these solvates may, for example, be hydrates or alcoholates.

Compounds of formula (I), which act as adenosine receptor agonists, are useful in the treatment of central nervous system conditions such as anxiety, neuronal ischaemia/anoxia, convulsive disorders (epilepsy) and neurodegeneration (including Parkinson's disease) in humans. This includes treating disorders where the blood flow to the brain is interrupted, for example during traumatic head injury, cardiac arrest and stroke. Further, the compounds of formula (I) are useful as analgesic agents, in lowering plasma free fatty acid (FFA) levels or as cardiovascular agents, e.g. treatment of myocardial ischaemia.

The compounds according to the invention are prepared as follows:

General Method A

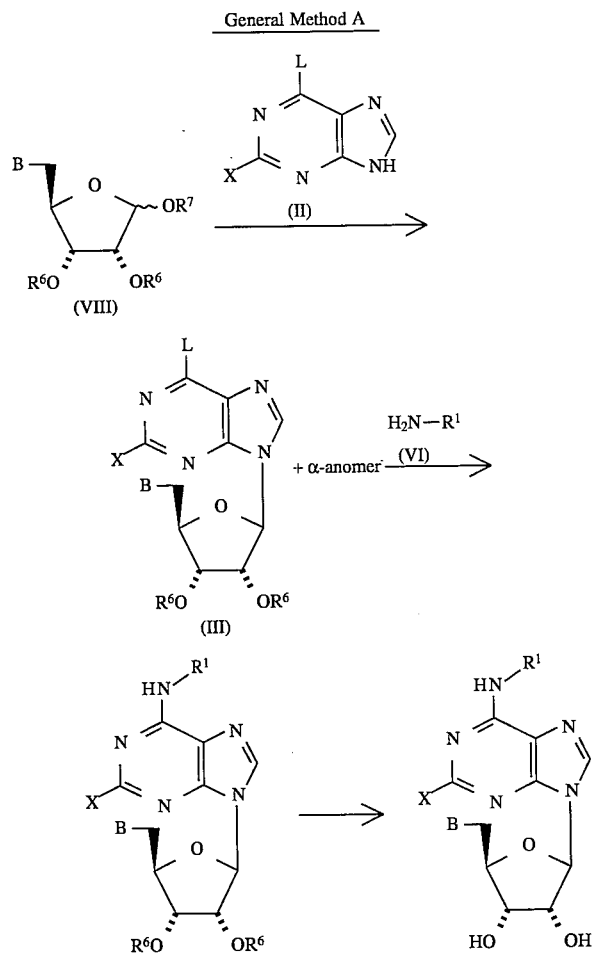

A compound of general formula (V) may be prepared by reacting a substance of general formula (VIII) (prepared according to general method B), where B represents a hydrogen, a halogen, a pseudohalogen, an alkoxy, or a thioalkoxy group and $R^6$ and $R^7$ represent hydrogen or a hydroxyl protecting group such as benzoyl, p-toluyl, lower alkanoyl, an alkylated silyl group, or alternatively the two $R^6$ may together represent a 1-methylethylidene with $R^7$ being defined as above, with a purine derivative (II) where X and L each represents a halogen, an alkoxy or a thioalkoxy group or a (protected) amino group, giving the reaction product (III) alone or together with the corresponding α-anomer. Substitution of L in compound (III) with an alkylated amine, an alkylated hydroxylamine or a functionalised hydrazine of general formula (VI) will give compound (IV). The corresponding α-anomer of compound (III) may be reacted in a similar way. Depending upon the nature of group $R^6$ deprotection of a compound of formula IV can be performed according to the art known (Greene, T. W., Protective Groups in Organic Synthesis, 2nd ed., 1991), to give a compound of formula V, which is a compound of formula I,

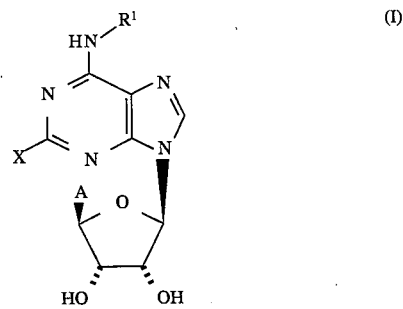

wherein A is methyl, chloromethyl, fluoromethyl, cyanomethyl, aminomethyl, methylthiomethyl or methoxymethyl.

General Method B:

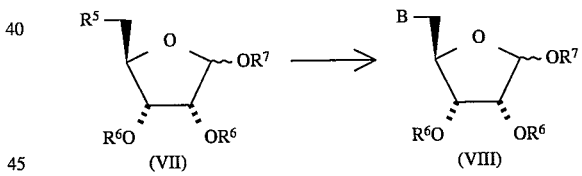

A compound of formula (VIII) where B, $R^6$ and $R^7$ are defined as in general method A, can be prepared from a compound (VII), where $R^6$ and $R^7$ are defined as in formula (I) and $R^5$ represents a hydroxy group or a suitable leaving group such as a halogen or a halogenated sulphonate. In cases where $R^5$ represents a hydroxy group, this can be directly alkylated to an alkoxy group with an alkylating reagent, or it can be halogenated with a suitable halogenation reagent to give compound (VIII). Alternatively, the group B may be introduced by reacting a compound (VII) where $R^5$ represents a leaving group, with a nucleophilic reagent containing nucleophiles such as an alkoxide, thioalkoxide, or halide (incl. pseudohalides). In cases where B represents a hydrogen, this may be introduced by reduction of compound (VII) where $R^5$ represents a hydroxyl or a suitable leaving group with a reducing reagent. The protecting groups $R^6$ and $R^7$ can be removed as described (Greene, T. W., Protective Groups in Organic Synthesis, 2nd ed. 1991).

General Method C:

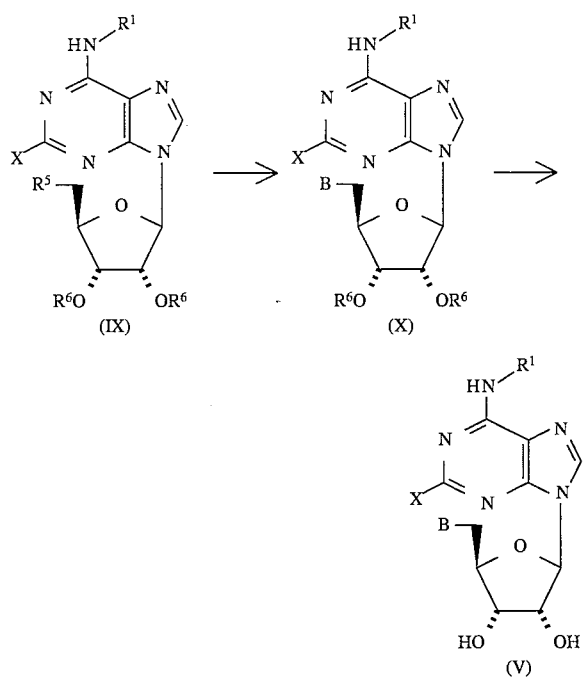

A compound of formula (V) where B, X and R¹ are defined as in general method A, can be prepared from a compound (IX) where $R^6$ is defined as in formula (VIII) and $R^5$ represents a hydroxy group or a suitable leaving group such as a halogen or an halogenated sulphonate. In cases where $R^5$ represents a hydroxy group this can be directly alkylated to an alkoxy group with an alkylating reagent, or it can be halogenated with a suitable halogenation reagent to give compound (X). Alternatively, the group B may be introduced by reacting a compound (IX) where $R^5$ represents a leaving group with a nucleophilic reagent containing nucleophiles such as an alkoxide, thioalkoxide, or halide (incl. pseudohalides).

In cases where B represents a hydrogen this may be introduced by reduction of compound (IX) where $R^5$ represents a hydroxyl or a suitable leaving group, with a reducing reagent. The protecting groups $R^6$ of formula (X) can be removed as described in the art known (Greene, T. W., Protective Groups in Organic Synthesis, 2nd ed 1991), to give a compound of formula V, which is a compound of formula I, .

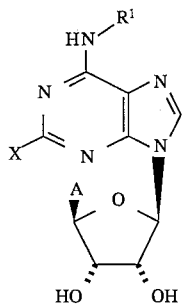
(I)

wherein A is methyl, chloromethyl, fluoromethyl, cyanomethyl, aminomethyl, methylthiomethyl or methoxymethyl.

Methods for assessing adenosine receptor binding in vitro have been reviewed [Adenosine Receptors, Cooper, D. M. F. and Londos, C., Eds., Alan R. Liss, Inc.: New York, 1988, 43–62].

Evaluation of these compounds in established animal models has indicated that the compounds according to the invention possess desirable central nervous system properties. For example, they act as anticonvulsant agents, are effective in animal models of pain, and show cerebroprotective effects in laboratory test animals subjected to simulated cerebral ischaemia. In addition, the compounds may have efficacy as neuroprotective agents in cases of cerebral oedema and traumatic head injury.

Evaluation of in vitro binding to adenosine $A_1$ and $A_2$ receptors.

The affinity of the novel compounds described in this invention for the adenosine $A_1$ receptor was determined essentially as described in the literature using [³H]-R-PIA as a radioligand (Naunyn-Schmiedeberg's Archives of pharmacology, 1980, 313, 179–187). Affinity for the $A_2$ receptor was measured using the radioligand [³H]-CGS 21680 (European Journal of Pharmacology, 1989, 168, 243–246), and the values for representative compounds is given in the table below. In vitro receptor binding values obtained for the reference standards CPA [N-(cyclopentyl)adenosine] and R-PIA [(R)-N-(1-phenyl-2-propyl)adenosine]) are included for comparison. The methods both for the above in vitro examination of the compounds and the method used for DMCM-induced seizures in vivo are summarized in the European Journal of Pharmacology, 1993, 224, 221–228.

The results obtained by testing selected compounds disclosed in the present invention are shown in the table I.

TABLE I

| Adenosine agonist tested | $A_1$ Receptor Binding (Ki, nM) | $A_2$ Receptor Binding (Ki, nM) | Ratio $A_2/A_1$ | DMCM-ind. seizures (ED$_{50}$, mg/kg) |
|---|---|---|---|---|
| Example 1 | 6.4 | 2739 | 428 | 0.4 |
| Example 11 | 11 | 6600 | 600 | 4.7 |
| Example 12 | 74 | 4655 | 63 | 6.1 |
| Example 18 | 5.3 | 2420 | 457 | 1.0 |
| CPA | 1.2 | 192 | 77 | 0.2 |
| R-PIA | 1.9 | 116 | 61 | 0.5 |

The compounds of the invention, together with a conventional adjuvant, carrier or diluent, and if desired in the form of a pharmaceutically acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of the adenosine receptor agonist commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

Active compound 5.0 mg

Lactosum 67.0 mg Ph. Eur.

Avicel™ 31.4 mg

Amberlite™IRP 88 1.0 mg

Magnesii stearas 0.25 mg Ph. Eur.

Owing to activity against pain or convulsive disorders and prevention of neurodegeneration under conditions of anoxia/ischaemia the compounds of the invention are extremely useful in the treatment of related symptoms in mammals, when administered in an amount effective for agonist activity of compounds of the invention. The compounds of the invention may accordingly be administered to a subject, e.g., a living animal body, including a human, in need of adenosine receptor agonist, and if desired in the form of a pharmaceutically acceptable acid addition salt thereof (such as the hydrobromide, hydrochloride, or sulphate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount of adenosine receptor agonist, and in any event an amount which is effective for the treatment of anoxia, traumatic injury, ischemia, migraine or other pain symptoms, epilepsy, or neurodegenerative diseases owing to their adenosine receptor agonist activity. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The preparation of compounds of formula (I) is further illustrated in the following examples.

Hereinafter, TLC is thin layer chromatography, THF is tetrahydrofuran, TFA is trifluoracetic acid and mp is melting point. Where melting points are given, these are uncorrected. The structures of the compounds are confirmed by assignment of NMR spectra (from which representative peaks are quoted) and by microanalysis where appropriate. Compounds used as starting materials are either known compounds or compounds which can be prepared by methods known per se. Column chromatography was carried out on Merck silica gel 60 interfaced via a system module to a Waters 490 multiwavelength detector to a reversed phase C18 column (250×4 mm, 5 µm, 100 Å; eluent flow rate 1 mL/min at 35° C). Retention times are given in minutes.

EXAMPLE 1

2,5'-Dichloro-5'-deoxy-N-(1-piperidinyl)adenosine

The title compound was prepared according to general method C.

2,5'-Dichloro-5'-deoxy-2',3'-O-(1-methylethylidene)-N-(1-piperidinyl)adenosine

2-Chloro-2',3'-O-(1-methylethylidene)-N-(1-piperidinyl)adenosine[prepared by protection of 2-Chloro-N-(1-piperidinyl)adenosine (Knutsen, L. J. S., Lau, J., Sheardown, M. J., Thomsen, C.; Bioorganic and Medicinal Chemistry Letters, 1993, 3, 2661–2666)] (0.28 g, 0.47 mmol), triphenylphosphine (0.31 g, 1.18 mmol) and tetrachloromethane (0.18 g, 1.18 mmol) was stirred in dry dimethylformamide (10 ml) at 20° C for 48 h. The reaction mixture was concentrated in vacuo and the crude product was purified by flash chromatography eluting with dichloromethane and 10% ammonia in ethanol (95:5) to give 2,5'-dichloro-5'-deoxy-2',3'-O-(1-methylethylidene)-N-(1-piperidinyl)adenosine (0.10 g, 48%) as a foam. $^1$H-NMR (400 MHz, DMSO-$d_6$) δ1.34 (3H, s, —CH$_3$), 1.36 (2H, m, piperidine C—H), 1.62 (4H, m, piperidine C—H), 2.82 (4H, br, piperidine C—H), 3.78, 3.88 (2H, ABX, H-5'$_a$ and H-5'$_b$), 4.35 (1H, ddd, H-4'), 5.02 (1H, dd, H-3'), 5.39 (1H, dd, H-2'), 6.20 (1H, d, H-1'), 8.36 (1H, s, H-8). HPLC retention time 21.45 min. (gradient elution over 30 min.; 20–80% acetonitrile/0.1% TFA in water).

Deprotection of 2,5'-dichloro-5'-deoxy-2',3'-O-(1-methylethylidene)-N-(1-piperidinyl)adenosine (0.11 g, 0.25 mmol) was performed by dissolving the compound in a mixture of ethanol (5 ml) and sulphuric acid (0.2M, 5 ml) and stirring the mixture for 72 h. at room temperature. The reaction mixture was neutralized with aqueous sodium bicarbonate and extracted with dichloromethane (3×50 ml). The organic phase was dried (MgSO$_4$) and evaporated in vacuo. The product was purified by flash chromatography on silica gel, eluting with a mixture of dichloromethane and 10% ammonia solution in ethanol (9:1), to provide the title 2,5'-dichloro-5'-deoxy-N-(1-piperidinyl)adenosine (0.1 g, 99%) as a foam, $^1$H-NMR (400 MHz, DMSO-$d_6$) δ1.35 (2H, br, piperidine C—H), 1.62 (4H, br, piperidine C—H), 2.80 (4H, br, piperidine C—H), 3.82, 3.93 (1H, ABX, H-5'$_a$ and H-5'$_b$), 4.10 (1H, dd, H-4'), 4.18 (1H, dd, H-3'), 4.63 (1H, dd, H-2'), 5.88 (1H, d, H-1'), 8.39 (1H, s, H-8). HPLC retention time 10.95 min. (gradient elution over 30 min.; 20–80% acetonitrile/0.1% TFA in water, 99% purity at 250 nm).

EXAMPLE 2

(S)-2,5'-Dichloro-5'-deoxy-N-[2-(methylmethoxy)-1-pyrrolidinyl]adenosine

The title compound was prepared according to general method C. (S)-2-Chloro-N-[2-(methylmethoxy)-1-pyrrolidinyl]adenosine [Knutsen, L. J. S., Lau, J., Sheardown, M. J., Thomsen, C.; Bioorganic and Medicinal Chemistry Letters, 1993, 3, 2661–2666](0.35 g, 0.8 mmol) was dissolved in acetonitrile (5 ml) and cooled on an ice-water bath. Under a nitrogen atmosphere, thionyl chloride (0.34 g, 0.2 ml, 2.4 mmol) (see Borchardt, R. T., Huber, J. A. and Wu, Y. S., Journal of Organic Chemistry, 1976, 41, 565–567) was added and a precipitate appeared which dissolved over the following 15 min. Pyridine (0.13 ml, 0.13 g, 1.6 mmol) was introduced gradually, the reaction mixture became yellow in colour and was allowed to reach room temperature gradually. After stirring the mixture overnight, ice was added and the reaction mixture was neutralised to pH 7 with aqueous sodium bicarbonate prior to extraction with ethyl acetate (2×10 ml). The combined extracts were dried ($MgSO_4$) and evaporated to provide the intermediate 2,3-O-sulphinyl derivative (0.35 g), to which was added methanol (5 ml), water (1 ml) and 25% aqueous ammonia solution (0.25 ml) and this mixture was stirred for 16 h. The solution was evaporated in vacuo, and the resultant residue was purified by flash chromatography on silica gel eluting with a mixture of dichloromethane and 10% ammonia in ethanol (17:3), to provide the title (S)-2,5'-dichloro-5'-deoxy-N-[2-(methylmethoxy)-1-pyrrolidinyl]adenosine (0.12 g, 34%) as a foam, $^1$H-NMR (400 MHz, DMSO-$d_6$) δ1.50–1.60 (1H, br, pyrrolidine C—H), 1.78 (2H, br q, pyrrolidine C—H), 1.92–2.03 (1H, br, pyrrolidine C—H), 3.85, 3.95 (2H, ABX, H-5'$_a$ and H-5'$_b$), 4.09 (1H, br dd, H-4'), 4.17 (1H, dd, H-3'), 4.67 (1H, dd, H-2'), 5.49, 5.62 (2H, 2d, 2'- and 3'-OH), 5.87 (1H, d, H-1'), 8.38 (1H, s, H-8), 9.34 (1H, br s, —NH). HPLC retention time 9.65 min. (gradient elution over 30 min.; 20–80% acetonitrile/0.1% TFA in water, 99% purity at 250 nm). $C_{16}H_{22}Cl_2N_6O_4 \cdot 0.25\ H_2O$ requires C, 43.9; H, 5.2; N, 19.2. Found: C, 43.7; H, 5.4; N, 19.4%.

EXAMPLE 3

2,5'-Dichloro-5'-deoxy-N-(4-phenoxy-1-piperidinyl)adenosine

This compound was prepared by general method C, described in more detail in Example 2. 2-Chloro-N-(4-phenoxy-1-piperidinyl)adenosine [WO 93/08206 (Novo Nordisk A/S)] (0.5 g, 1.05 mmol) was subjected to the chlorination conditions described above, providing the title compound 2,5'-dichloro-5'-deoxy-N-(4-phenoxy-1-piperidinyl)adenosine which precipitated on treatment with dichloromethane following trituration with ether. Drying in vacuo provided a solid (0.28 g, 56%), m.p. 165°–170° C., $^1$H-NMR (400 MHz, DMSO-$d_6$) δ1.74–1.84 (2H, br, piperidine C—H), 1.99–2.08 (2H, br, piperidine C—H), 2.80–2.90 (2H, br, piperidine C—H), 3.04–3.12 (2H, br, piperidine C—H), 3.85, 3.94 (2H, ABX, H-5'$_a$ and H-5'$_b$), 4.09 (1H, q, H-4'), 4.18 (1H, q, H-3'), 4.44 (1H, br, PhO—C—H) 4.66 (1H, dd, H-2'), 5.50, 5.63 (2H, 2d, 2'- and 3'-OH), 5.89 (1H, d, H-1'), 6.94 (1H, t, Ar—H), 6.99 (2H, d, Ar—H), 7.30 (2H, t, Ar—H), 8.40 (1H, s, H-8). HPLC retention time 19.15 min. (gradient elution over 30 min.; 20–80% acetonitrile/0.1% TFA in water, 99.9% purity at 250 nm).

EXAMPLE 4

2,5'-Dichloro-5'-deoxy-N-(3-methoxy-1-piperidinyl)adenosine

This compound was prepared by general method C, described in more detail in Example 2. 2-Chloro-N-(3-methoxy-1-piperidinyl)adenosine (prepared by O-methylation of N-tertbutyloxycarbonyl-3-hydroxypiperidine, followed by use of the N-amination technique described in Overberger, C. G. and Herin, L. P. Journal of Organic Chemistry, 1962, 27, 417, and further reaction of the resultant hydrazine as described in Knutsen, L. J. S., Lau, J., Sheardown, M. J., Thomsen, C.; Bioorganic and Medicinal Chemistry Letters, 1993, 3, 2661–2666) (0.1 g, 0.24 mmol) was subjected to the chlorination conditions described in Example 2, providing the title 2,5'-dichloro-5'-deoxy-N-(3-methoxy-1-piperidinyl)adenosine (mixture of diastereoisomers) (0.07 g, 67%), following column chromatography, as a solid, m.p. 200°–202° C. $^1$H-NMR (400 MHz, DMSO-$d_6$) δ3.86, 3.94 (2H, ABX, H-5'$_a$ and H-5'$_b$), 4.11 (1H, q, H-4'), 4.19 (1H, q, H-3'), 4.65 (1H, dd, H-2'), 5.49, 5.62 (2H, 2d, 2'- and 3'-OH), 5.88 (1H, d, H-1), 8.39 (1H, s, H-8). HPLC retention time 17.08 min. (gradient elution over 30 min.; 20–80% acetonitrile/0.1% TFA in water, 98.7% purity at 250 nm).

EXAMPLE 5

2,5'-Dichloro-5'-deoxy-N-(4-phenylthio-1-piperidinyl)adenosine

This compound was prepared by general method C, described in more detail in Example 2. 2-Chloro-N-(4-phenylthio-1-piperidinyl)adenosine [WO 93/08206 (Novo Nordisk A/S)] (5.49 g, 11.1 mmol) was subjected to the reaction conditions described above, providing the title 2,5'-di-chloro-5'-deoxy-N-(4-phenylthio-1-piperidinyl)adenosine which precipitated from the aqueous methanolic ammonia. Recrystallization provided a solid (3.93 g, 69%), m.p. 154°–157° C., $^1$H-NMR (400 MHz, DMSO-$d_6$) δ1.74–1.84 (2H, br, piperidine C—H), 1.95–2.05 (2H, br, piperidine C—H), 2.80–2.90 (1H, br, piperidine C—H), 3.04–3.12 (2H, br, piperidine C—H), 3.84, 3.93 (2H, ABX, H-5'$_a$ and H-5'$_b$), 4.10 (1H, q, H-4'), 4.17 (1H, q, H-3'), 4.64 (1H, dd, H-2'), 5.48, 5.62 (2H, 2d, 2'- and 3'-OH), 5.87 (1H, d, H-1'), 7.26 (1H, t, Ar—H), 7.35 (2H, t, Ar—H), 7.42 (2H, d, Ar—H), 8.38 (1H, s, H-8), 9.49 (1H, s, N—H). HPLC retention time 22.19 min. (gradient elution over 30 min.; 20–80% acetonitrile/0.1% TFA in water, 100% purity at 250 nm).

EXAMPLE 6

2,5'-Dichloro-5'-deoxy-N-(3-phenylthio-1-piperidinyl)adenosine

This compound was prepared by general method C, described in more detail in Example 2. 2-Chloro-N-(4-phenylthio-1-piperidinyl)adenosine [WO 93/08206 (Novo Nordisk A/S)] (0.5 g, 1 mmol) was subjected to the reaction conditions described above, providing the title 2,5'-dichloro-5'-deoxy-N-(3-phenylthio-1-piperidinyl)adenosine (mixture of diastereoisomers) as a foam (0.48 g, 94%) following flash chromatography on silica gel. $^1$H-NMR (400 MHz, DMSO- $d_6$) δ3.84, 3.92 (2H, ABX, H-5'$_a$ and H-5'$_b$), 4.10 (1H, q, H-4'), 4.17 (1H, q, H-3'), 4.64 (1H, dd, H-2'), 5.49, 5.62 (2H, 2d, 2'- and 3'-OH), 5.87 (1H, d, H-1'), 7.22 (1H, t, Ar—H), 7.31 (2H, t, Ar—H), 7.43 (2H, d, Ar—H), 8.39 (1H, s, H-8). HPLC retention time 17.08 min. (gradient elution over 30 min.; 20–80% acetonitrile/0.1% TFA in water, 98.7% purity at 250 nm).

EXAMPLE 7

2,5'-Dichloro-5'-deoxy-N-(4-phenylsulphinyl-1-piperidinyl)adenosine

2',3'-Di-O-acetyl-2,5'-dichloro-5'-deoxy-N-(4-phenylthio-1-piperidinyl)adenosine (prepared by acetylation of Example 5) (2.95 g, 5 mmol) was dissolved in dry dichloromethane (100 ml). "Oxone" (7.7 g, 2.5 equiv.) and wet clay (Hirano, M., Tomaru, J. and Morimoto, T. Bull. Chem. Soc. Japan, 1991, 64, 3752–3754) (5.95 g) were introduced with vigourous stirring. Both the phenylsulphinyl product ($R_f$=0.21) and the phenylsulphonyl product ($R_f$=0.45) were apparent by TLC [SiO$_2$, ethyl acetate/methanol (9:1)] and after 0.5 h. reaction time the reaction mixture was filtered. The filtrate was washed with water (2×100 ml), dried (MgSO$_4$) and evaporated. The residue was purified by flash chromatography on silica gel eluting with a mixture of ethyl acetate and heptane (1:1), then with ethyl acetate, and finally with a mixture of ethyl acetate and methanol (19:1), to provide 2',3'-di-O-acetyl-2,5'-dichloro-5'-deoxy-N-(4-phenylsulphinyl-1-piperidinyl)adenosine (0.18 g, 6%) and 2',3'-di-O-acetyl-2,5'-dichloro-5'-deoxy-N-(4phenylsulphonyl-1-piperidinyl)adenosine (1.2 g, 39%) as foams.

5'-Deoxy-2,5'-dichloro-N-(4-phenylsulphinyl-1-piperidinyl)adenosine

2',3-Di-O-acetyl-2,5'-dichloro-5'-deoxy-N-(4-phenylsulphinyl-1-piperidinyl)adenosine (0.22 g, 0.36 mmol) was dissolved in methanol (10 ml) and methanolic ammonia (1 ml) was introduced. After 1 h. at room temperature, the reaction mixture was evaporated to a residue and purified by flash chromatography on silica gel, eluting with a mixture of dichloromethane and ethanol (9:1) to provide 2,5'-dichloro-5'-deoxy-N-(4-phenylsulphinyl-1-piperidinyl)adenosine (0.1 g, 53%) as a foam.

$^1$H-NMR (400 MHz, DMSO-d$_6$) δ3.84, 3.93 (2H, ABX, H-5'$_a$ and H-5'$_b$), 4.10 (1H, q, H-4'), 4.17 (1H, q, H-3'), 4.63 (1H, dd, H-2'), 5.49, 5.62 (2H, 2d, 2'- and 3'-OH), 5.87 (1H, d, H-1'), 7.53–7.66 (5H, m, Ar—H), 8.38 (1H, s, H-8). HPLC retention time 14.24 min. (gradient elution over 30 min.; 20–80% acetonitrile/0.1% TFA in water, 95.4% purity at 250 nm).

EXAMPLE 8

2,5'-Dichloro-5'-deoxy-N-(4-phenylsulphonyl-1-piperidinyl)adenosine

2',3-Di-O-acetyl-2,5'-dichloro-5'-deoxy-N-(4-phenylsulphonyl-1-piperidinyl)adenosine (generated during the preparation of Example 7) (1.2 g, 1.9 mmol) was dissolved in methanol (90 ml) and methanolic ammonia (10 ml) was introduced. After 0.5 h. at room temperature, the reaction mixture was evaporated to a residue and purified by flash chromatography on silica gel, eluting with a mixture of dichloromethane and ethanol (9:1) to provide 2,5'-dichloro-5'-deoxy-N-(4-phenylsulphonyl-1-piperidinyl)adenosine (0.82 g, 79%) as a foam. $^1$H-NMR (400 MHz, DMSO-d$_6$) δ3.84, 3.93 (2H, ABX, H-5'$_a$ and H-5'$_b$), 4.09 (1H, dt, H-4'), 4.16 (1H, ps t, H-3'), 4.62 (1H, dd, H-2'), 5.49, 5.62 (2H, 2d, 2'- and 3'-OH), 5.87 (1H, d, H-1'), 7.71 (2H, t, Ar—H), 7.80 (1H, t, Ar—H), 7.90 (1H, d, Ar—H), 8.39 (1H, s, H-8). HPLC retention time 13.78 min. (gradient elution over 30 min.; 20–80% acetonitrile/0.1% TFA in water, 96.9% purity at 250 nm).

EXAMPLE 9

2,5'-Dichloro-5'-deoxy-N-(4-phenyl-1-piperidinyl)adenosine

This compound was prepared by general method C, described in more detail in Example 2. 2-Chloro-N-(4-phenyl-1-piperidinyl)adenosine [WO 93/08206 (Novo Nordisk A/S)] (0.3 g, 0.65 mmol) was subjected to the chlorination conditions described above, providing the title 2,5'-dichloro-5'-deoxy-N-(4phenyl-1-piperidinyl)adenosine as a foam (0.28 g, 90%), $^1$H-NMR (400 MHz, DMSO-d$_6$) δ3.86, 3.95 (2H, ABX, H-5'$_a$ and H-5'$_b$), 4.11 (1H, q, H-4'), 4.21 (1H, q, H-3'), 4.66 (1H, dd, H-2'), 5.49, 5.63 (2H, 2d, 2'- and 3'-OH), 5.89 (1H, d, H-1'), 7.20 (1H, dt, Ph—C—H), 7.31 (5H, d, Ar—H), 8.40 (1H, s, H-8), 9.45 (1H, s, N—H). HPLC retention time 20.92 min. (gradient elution over 30 min.; 20–80% acetonitrile/0.1% TFA in water, 99.75% purity at 250 nm).

EXAMPLE 10

2,5'-Dichloro-5'-deoxy-N-(4-phenyl-1-piperidinyl)adenosine

This compound was prepared by the method described in Example 2. 2-Chloro-N-(1-morpholinyl)adenosine [WO 93/08206 (Novo Nordisk A/S)] (1.0 g, 2.6 mmol) was subjected to the chlorination conditions described above, providing the title 2,5'-dichloro-5'-deoxy-N-(1-morpholinyl)adenosine as a foam (0.78 g, 74%), $^1$H-NMR (400 MHz, DMSO-d$_6$) δ2.38 (4H, br, morpholine C—H), 3.71 (4H, br, morpholine C—H), 3.85, 3.94 (2H, ABX, H-5'$_a$ and H-5'$_b$), 4.10 (1H, q, H-4'), 4.18 (1H, q, H-3'), 4.64 (1H, q, H-2'), 5.50, 5.63 (1H, 2d, 2'-and 3'-OH), 5.88 (1H, d, H-1'), 8.41 (1H, s, H-8), 9.50 (1H, s, NH). HPLC retention time 7.82 min. (gradient elution over 30 min.; 20–80% acetonitrile/ 0.1% TFA in water, 97.8% purity at 250 nm). $C_{14}H_{18}Cl_2N_6O_4 \cdot 0.5$ EtOH requires C, 42.1; H, 4.9; N, 19.6. Found: C, 41.6; H, 5.2; N, 19.0%.

EXAMPLE 11

2,5'-Dichloro-5'-deoxy-N-(dimethylamino)adenosine

This compound was prepared by general method C, described in more detail in Example 2. 2-Chloro-N-(dimethylamino)adenosine [WO 93/23417 (Novo Nordisk A/S)] (0.62 g, 1.8 mmol) was subjected to the chlorination conditions described above, providing the title 2,5'-dichloro-5'-deoxy-N-(dimethylamino)adenosine as a solid (0.23 g, 41%) after column chromatography, m.p. 188°–189° C., $^1$H-NMR (400 MHz, DMSO-d$_6$) δ2.59 (6H, s, N(CH$_3$)$_2$), 3.85, 3.94 (2H, ABX, H-5'$_a$ and H-5'$_b$), 4.10 (1H, q, H-4'), 4.18 (1H, q, H-3'), 4.66 (1H, q, H-2'), 5.50, 5.62 (1H, 2d, 2'-and 3'-OH), 5.88 (1H, d, H-1'), 8.38 (1H, s, H-8), 9.39 (1H, br, NH). $C_{12}H_{16}Cl_2N_6O_3 \cdot 0.25$ H$_2$O. 0.25 EtOH requires C, 39.6; H, 4.8; N, 22.2. Found: C, 39.5; H, 4.5; N, 22.3%.

EXAMPLE 12

2,5'-Dichloro-5'-deoxy-N-methoxyadenosine

This compound was prepared by the method described in Example 2. 2-Chloro-N-(methoxy)adenosine [WO 93/23417 (Novo Nordisk A/S)] (0.8 g, 2.4 mmol) was subjected to the chlorination conditions described above, providing the title 2,5'-dichloro-5'-deoxy-N-methoxyadenosine as a foam (0.34 g, 40%), $^1$H-NMR (400 MHz, DMSO-$d_6$) δ3.78 (3H, s, —OCH$_3$), 3.85, 3.94 (2H, ABX, H-5'$_a$ and H-5'$_b$), 4.10 (1H, q, H-4'), 4.19 (1H, q, H-3'), 4.66 (1H, q, H-2'), 5.51, 5.65 (1H, 2d, 2'-and 3'-OH), 5.90 (1H, d, H-1'), 8.45 (1H, s, H-8), 11.59 (1H, s, NH). HPLC retention time 6.99 min. (gradient elution over 30 min.; 20–80% acetonitrile/0.1% TFA in water, 96.5% purity at 250 nm).

EXAMPLE 13

N-Cyclopentoxy-2,5'-dichloro-5'-deoxy-adenosine

This compound was prepared by general method C, described in more detail in Example 2. N-Cyclopentoxy-2-chloroadenosine [WO 93/23417 (Novo Nordisk A/S)] (1.0 g, 2.6 mmol) was subjected to the chlorination conditions described above, providing the title N-cyclopentoxy-2,5'-dichloro-5'-deoxy-adenosine as a foam (0.82 g, 78%), $^1$H-NMR (400 MHz, DMSO-$d_6$) δ1.49–1.92 (8H, 3m, cyclopentyl C—H), 3.86, 3.94 (2H, ABX, H-5'$_a$ and H-5'$_b$), 4.11 (1H, q, H-4'), 4.20 (1H, q, H-3'), 4.59 (1H, m, —OC—H), 4.67 (1H, q, H-2'), 5.51, 5.64 (1H, 2d, 2'-and 3'-OH), 5.90 (1H, d, H-1'), 8.44 (1H, s, H-8), 11.44 (1H, s, NH). HPLC retention time 12.2 min. (gradient elution over 30 min.; 20–80% acetonitrile/0.1% TFA in water, 97.4% purity at 250 nm). $C_{15}H_{19}Cl_2N_5O_4 \cdot 0.5$ EtOH requires C, 45.0; H, 5.2; N, 16.4. Found: C, 45.2; H, 5.1; N, 16.2%.

EXAMPLE 14

2-Bromo-5'-chloro-5'-deoxy-N-(1-piperidinyl)adenosine

This compound was prepared by general method C, described in more detail in Example 2. 2-Bromo-N-(1-piperidinyl)adenosine [WO 93/23417 (Novo Nordisk A/S)] (0.06 g, 0.14 mmol) was subjected to the chlorination conditions described above, providing the title 2-bromo-5'-chloro-5'-deoxy-N-(1-piperidinyl)adenosine as a foam (0.016 g, 26%), $^1$H-NMR (400 MHz, DMSO-$d_6$) δ1.37 (2H, br, piperidine C—H), 1.64 (4H, br, piperidine C—H), 2.80 (4H, br, piperidine C—H), 3.85, 3.93 (2H, ABX, H-5'$_a$ and H-5'$_b$), 4.09 (1H, q, H-4'), 4.18 (1H, q, H-3'), 4.65 (1H, q, H-2'), 5.48, 5.62 (1H, 2d, 2'-and 3'-OH), 5.87 (1H, d, H-1'), 8.33 (1H, s, H-8), 9.36 (1H, s, NH). HPLC retention time 9.65 min. (gradient elution over 30 min.; 20–80% acetonitrile/0.1% TFA in water, 94% purity at 250 nm).

EXAMPLE 15

2-Amino-5'-chloro-5'-deoxy-N-(4-phenylthio-1-piperidinyl)adenosine

This compound was prepared by general method C, described in more detail in Example 2. 2-Amino-N-(4-phenylthio-1-piperidinyl)adenosine [prepared by reaction of 9-(2,3,5-tri-O-acetyl-β-D-ribofuranosyl)-9H-2-amino-6-chloro-9H-purine (Knutsen, L. J. S., Lau, J., Sheardown, M. J., Thomsen, C.; Bioorganic and Medicinal Chemistry Letters, 1993, 3, 2661–2666) with 1-amino-4-phenylthiopiperidine] (0.47 g, 1.0 mmol) was subjected to the chlorination conditions described above. Column chromatography on silica gel, eluting initially with a mixture of heptane and ethyl acetate (7:3), increasing polarity to pure ethyl acetate provided the title 2-amino-5'-chloro-5'-deoxy-N-(4-phenylthio-1-piperidinyl)adenosine (0.1 g, 20%) as a foam. $^1$H-NMR (400 MHz, DMSO-$d_6$) δ1.65 (2H, dq, piperidine C—H), 1.91–2.01 (2H, br, piperidine C—H), 2.75 (2H, br t, piperidine C—H), 2.98–3.07 (2H, br, piperidine C—H), 3.82, 3.92 (2H, ABX, H-5'$_a$ and H-5'$_b$), 4.04 (1H, dt, H-4'), 4.15 (1H, q, H-3'), 4.64 (1H, dd, H-2'), 5.36, 5.52 (2H, 2d, 2'- and 3'-OH), 5.77 (1H, d, H-1'), 5.96 (1H, br s, —NH$_2$), 7.27 (1H, t, Ar—H), 7.37 (2H, t, Ar—H), 7.42 (2H, d, Ar—H), 7.91, 8.18 (2H, 2s, H-8, N—H).

EXAMPLE 16

5'-Chloro-5'-deoxy-2-methylthio-N-(1-piperidinyl)adenosine

This compound was prepared by general method C, described in more detail in Example 2. 2-Methylthio-N-(1-piperidinyl)adenosine [WO 93/23417 (Novo Nordisk A/S)] (0.15 g, 0.38 mmol) was subjected to the chlorination conditions described above, providing 5'-chloro-5'-deoxy-2-methylthio-N-(1-piperidinyl)adenosine as a solid (0.07 g, 45%) mp 213°–215° C. $^1$H-NMR (400 MHz, DMSO-$d_6$) δ1.37 (2H, br, piperidine C—H), 1.62 (4H, br q, piperidine C—H), 2.48 (3H, s, —SCH$_3$), 2.81 (4H, br, piperidine C—H), 3.83, 3.93 (2H, ABX, H-5'$_a$ and H-5'$_b$), 4.08 (1H, q, H-4'), 4.23 (1H, q, H-3'), 4.75 (1H, q, H-2'), 5.47, 5.59 (1H, 2d, 2'-and 3'-OH), 5.88 (1H, d, H-1'), 8.22 (1H, s, H-8), 8.85 (1H, s, NH). HPLC retention time 9.15 min. (gradient elution over 30 min.; 20–80% acetonitrile/0.1% TFA in water, 96.4% purity at 250 nm).

EXAMPLE 17

5'-Bromo-2-chloro-5'-deoxy-N-(1-piperidinyl)adenosine

This compound was prepared by general method C, described in more detail in Example 2. 2-Chloro-N-(1-piperidinyl)adenosine [WO 93/08206 (Novo Nordisk A/S)] (3.08 g, 8 mmol) was subjected to the same reaction conditions described above, except that thionyl bromide was substituted for thionyl chloride. The procedure provided the desired 5'-bromo-2-chloro-5'-deoxy-N-(1-piperidinyl)adenosine as a foam (0.19 g, 9%) after column chromatography, $^1$H-NMR (400 MHz, DMSO-$d_6$) δ1.37 (2H, br, piperidine C—H), 1.62 (4H, m, piperidine C—H), 2.80 (4H, br, piperidine C—H), 3.72, 3.82 (2H, ABX, H-5'$_a$ and H-5'$_b$), 4.10 (1H, dt, H-4'), 4.17 (1H, dt, H-3'), 4.68 (1H, q, H-2'), 5.50, 5.62 (1H, 2d, 2'- and 3'-OH), 5.88 (1H, d, H-1'), 8.38 (1H, s, H-8), 9.36 (1H, br, NH). HPLC retention time 11.06 min. (gradient elution over 30 min.; 20–80% acetonitrile/ 0.1% TFA in water, 96.4% purity at 250 nm). $C_{15}H_{20}N_6BrClO_3 \cdot 1.3$ H$_2$O requires C, 38.2; H, 4.8; N, 17.8. Found: C, 38.7; H, 4.7; N, 17.3%.

EXAMPLE 18

2-Chloro-5'-deoxy-5'-fluoro-N-(1-piperidinyl)adenosine

This compound was prepared using general method A starting from 1,2,3-tri-O-acetyl-5-deoxy-5-fluoro-D-ribofuranose prepared according to general method B.

Methyl 5-Deoxy-5-fluoro 2,3-O-(1-methylethylidene)-β-D-ribofuranoside

Methyl 2,3-O-(1-methylethylidene)-5-O-(p-toluenesulfonyl)-β-ribofuranoside (28.7 g, 80 mmol) was dissolved in dry acetonitrile (100 ml). Tetra-n-butylammonium fluoride (100 ml, 1.0M in THF) was added dropwise and the reaction mixture was heated at 80° C. for 72 h. After cooling to room temperature, the mixture was diluted with dichloromethane (200 ml), washed with water (3×50 ml) and dried ($MgSO_4$). Evaporation provided a residue which was purified by flash chromatography eluting with a mixture of ethyl acetate and n-heptane (1:3) to give methyl 5-deoxy-5-fluoro-2,3-O-(1-methylethylidene)-β-D-ribofuranoside (13.6 g, 82%) as a clear oil, $^1$H NMR ($CDCl_3$) δ1.34 (3H, s, $CH_3$), 1.50 (3H, s, $CH_3$), 3.35 (3H, s, —$OCH_3$), 4.29–4.48 (3H, m, H-4, H-5$_a$ and H-5$_b$), 4.60 (1H, d, H-3), 4.70 (1H, d, H-2), 4.99 (1H, d, H-1).

1,2,3-Tri-O-acetyl-5-deoxy-5-fluoro-β-D-ribofuranose

Methyl 5-deoxy-5-fluoro-2,3-O-(1-methylethylidene)-β-D-ribofuranoside (5.0 g, 24 mmol) was treated with sulfuric acid (0.02M, 40 ml) and heated at reflux for 4 h. The reaction mixture was cooled, neutralized with barium carbonate to pH 7, filtered and evaporated to an oil. The oil was dried by coevaporation with ethanol, and the residue was dissolved in dichloromethane (50 ml). Acetic anhydride (25 ml) and pyridine (25 ml) were introduced, and the reaction mixture was stirred for 16 h before being poured onto ice (100 ml). The cool suspension was extracted with dichloromethane (3×100 ml), and the combined extracts was washed with 2N hydrochloric acid solution (50 ml) and aqueous sodium bicarbonate solution (50 ml). The organic phase was dried ($MgSO_4$), evaporated in vacuo and the residue was purified by flash chromatography, eluting with a mixture of dichloromethane and 10% ammonia in ethanol (97:3) to provide 1,2,3-tri-O-acetyl-5-deoxy-5-fluoro-β-D-ribofuranose (5.3 g, 79%), which crystallized on standing.

Recrystallisation from absolute ethanol provided analytically pure material, m.p. 98°–101° C., $^1$H NMR ($CDCl_3$) δ2.09 (3H, s, —$OCOCH_3$), 2.10 (3H, s, —$OCOCH_3$), 2.14 (3H, s, —$OCOCH_3$), 4.34 (1H, ddd, H-4), 4.49 (1H, ddd, H-5$_a$), 4.52 (1H, ddd, H-5$_b$), 5.36 (1H, d, H-3), 5.46 (1H, dd, H-2), 6.17 (1H, s, H-1). $C_{11}H_{15}FO_7$ requires C, 47.5; H 5.4. Found: C, 47.7; H, 5.6%.

9[(2',3'-Di-O-acetyl-5'-deoxy-5'-fluoro-D-ribofuranosyl)]-2,6-dichloro-9H-purine A mixture of the above 1,2,3-tri-O-acetyl-5-deoxy-5-fluoro-D-ribofuranose (5.0 g, 18 mmol) and 2,6-dichloropurine (3.4 g, 18 mmol) was heated to 160° C. A catalytic amount of sulfuric acid (one drop) was added at which point a homogeneuos melt was obtained. The fusion was continued at 160° C. under oil pump vacuum for 0.5 h. After cooling, the reaction mixture was dissolved in chloroform (200 ml) and washed with aqueous sodium bicarbonate (3×50 ml) and water (50 ml). The organic phase was dried ($MgSO_4$) and evaporated in vacuo before purification by flash chromatography. Elution with a mixture of dichloromethane and 10% ammonia in ethanol (98:2) afforded an anomeric mixture of 9[(2',3'-di-O-acetyl-5'-deoxy-5'-fluoro-D-ribofuranosyl)]-2,6-dichloro-9H-purine (4.5 g, 90%) as a gum, $^1$H NMR (DMSO-$d_6$)δ(α-anomer) 1.84 (3H, s, —$OCOCH_3$), 2.00 (3H, s, —$OCOCH_3$), 4.71 (2H, dd, H-5'a, H-5'b), 5.98 (1H, ddd, H-4'), 5.48 (1H, t, H-3), 5.68 (1H, t, H-2'), 6.73 (1H, d, H-1'), 8.92 (1H, s, H-8); (β-anomer) 2.05 (3H, s, —$OCOCH_3$), 2.11 (3H, s, —$COCH_3$), 4.50 (1H, ddd, H-4), 4.77 (2H, dd, H-5'$_a$ and H-5'$_b$), 5.61 (1H, t, H-3), 5.89 (1H, t, H-2'), 6.33 (1H, d, H-1), 8.92 (1H, s, H-8).

2',3'-Di-O-acetyl-2-chloro-5'-deoxy-5'-fluoro-N-(1-piperidinyl)adenosine:

An α/β mixture of 9-[(2',3'-di-O-acetyl-5'-deoxy-5'-fluoro-D-ribofuranosyl])-2,6-dichloro-9H-purine (1.24 g, 3.0 mmol), N,N-diisopropylethyl amine (0.79 g, 6.1 mmol) and 1-aminopiperidine (0.60 g, 6.0 mmol) were stirred in dioxan (20 ml) for 4 h. The reaction mixture was diluted with dichloromethane (200 ml) and washed with water (2×50 ml). After drying over ($MgSO_4$) the organic phase was evaporated in vacuo and the residue was purified by flash chromatography. Elution with dichloromethane and 10% ammonia in ethanol (98:2) afforded the β-anomer of 2',3'-di-O-acetyl-2-chloro-5'-deoxy-5'-fluoro-N-(1-piperidinyl)adenosine (0.40 g, 28%) as a foam. HPLC retention time 14.8 min. (gradient elution over 30 min.; 20–80% acetonitrile/0.1% TFA in water).

The above 2',3'-di-O-acetyl-2-chloro-5'-deoxy-5'-fluoro-N-(1-piperidinyl)adenosine (0.38 g, 0.8 mmol) was dissolved in methanolic ammonia (15 ml) and stirred for 1 h. The reaction mixture was evaporated in vacuo and the resultant residue was purified by flash chromatography eluting with dichloromethane and 10% ammonia in ethanol (95:5) to afford 2-chloro-5'-deoxy-5'-fluoro-N-(1-piperidinyl)adenosine (1.8 g, 86%) as a white solid, m.p. 199°–201° C. $^1$H-NMR (400 MHz, DMSO-$d_6$) δ1.35 (2H, br, piperidine C—H), 1.52 (4H, br, piperidine C—H), 2.80 (4H, br, piperidine C—H), 4.10 (1H, ddd, H-4'), 4.20 (1H, br, H-3'), 4.51 (1H, br, H-2'), 4.65 (2H, dd, H-5'$_a$ and H-5'$_b$), 5.88 (1H, d, H-1'), 8.28 (1H, s, H-8). HPLC retention time 7.15 min. (gradient elution over 30 min.; 20–80% acetonitrile/0.1% TFA in water). $C_{15}H_{20}ClFN_6O_3$, 0.75$H_2O$ requires C, 45.2; H, 5.4; N, 21.1. Found: C, 45.2; H, 5.2; N, 20.8%.

EXAMPLE 19

2-Chloro-5'-deoxy-5'-fluoro-N-benzyloxyadenosine

This compound was prepared by general method A, described in more detail in Example 18 by reacting O-benzylhydroxylamine hydrochloride (0.80 g, 5.0 mmol) with 9-[(2',3'-di-O-acetyl-5'deoxy-5'-fluoro-D-ribofuranosyl)]-2,6-dichloro-9H-purine (1.0 g, 2.5 mmol) as described above. The product was purified by flash chromatography eluting with a mixture of dichloromethane and 10% ammonia in ethanol (98:2) giving the intermediate 2',3'-di-O-acetyl-2-chloro-5'-deoxy-5'-fluoro-N-benzyloxyadenosine (0.2 g, 16%). Deacetylation was performed in methanolic ammonia to afford 2-chloro-5'-deoxy-5'-fluoro-N-benzyloxyadenosine as a foam (0.11 g, 89%) after flash chromatography eluting with dichloromethane and 10% ammonia in ethanol (95:5). $^1$H-NMR (400 MHz, DMSO-$d_6$) δ4.12 (1H, m, H-4'), 4.20 (1H, m, H-3'), 4.53 (1H, m, H-2'), 4.65 (2H, dd, H-5'$_a$ and H-5'$_b$), 5.00 (2H, s, —$CH_2$—), 5.48, 5.60 (2H, 2d, 2'-and 3'-OH) 5.91 (1H, d, H-1'), 7.30–7.55 (5H, m, Ar—H), 8.43 (1H, s, H-8), 11.65 (1H, s, N—H). HPLC retention time 14.60 min. (gradient elution over 30 min,; 20–80% acetonitrile/0.1% TFA in water, 96% purity at 250 nm).

EXAMPLE 20

(S)-2-Chloro-5'-O-methyl-N-(2-(methylmethoxy)-1-pyrrolidinyl)adenosine

The title compound was prepared using general method A starting from 5-O-methyl-1,2,3-tri-O-acetyl-D-ribofuranose, itself prepared according to general method B.

Methyl 5-O-methyl-2,3-O-(1-methylethylidene)-β-D-ribofuranoside.

Methyl 2,3-O-(1-methylethylidene)-β-D-ribofuranoside (13.3 g, 60 mmol), 2,6-di-t-butyl-4-methylpyridine (20.0 g, 100 mmol) and methyl trifluoromethylsulfonate (16.0 g, 100 mmol) were dissolved in dry dichloromethane (150 ml) placed in a closed reactor and heated to 80° C. After cooling, the reaction mixture was poured onto ice (150 ml). After standing, the product was extracted into dichloromethane (2×100 ml) and the combined extracts were dried (MgSO$_4$) and evaporated in vacuo. The residue was purified by flash chromatography eluting with a mixture of cyclohexane and ethyl acetate (3:1) to afford methyl 5-O-methyl-2,3-O-(1-methylethylidene)-β-D-ribofuranoside (8.0 g, 61%) as an oil. $^1$H-NMR (400 MHz, CDCl$_3$) δ1.30 (3H, s, —CH$_3$), 1.50 (3H, s, —CH$_3$), 3.32 (3H, s, —OCH$_3$), 3.39 (3H, s, —OCH$_3$), 3.35–3.45 (2H, m, H-5$_a$ and H-5$_b$), 4.30 (1H, t, H-4), 4.57 (1H, d, H-3), 4.65 (1H, d, H-2), 4.97 (1H, s, H-1).

1,2,3-Tri-O-acetyl-5-O-methyl-β-D-ribofuranose.

5-O-Methyl-2,3-O-(1-methylethylidene)-β-D-ribofuranoside (3.0 g, 14 mmol) was dissolved in a mixture of sulfuric acid (0.02M, 100 ml) and ethanol (50 ml) and heated at 80° C. for 6 h and stirred for 20 h at 20° C. The reaction mixture was neutralised with aqueous sodium bicarbonate and concentrated in vacuo. The residual oil was dried and acetylated in a mixture of dichloromethane (100 ml), acetic anhydride (8.5 g, 83 mmol) and triethylamine (16.7 g, 165 mmol) at 20° C. for 20 h. The reaction mixture was washed with hydrochloric acid (1M, 50 ml) and water (50 ml). The organic phase was dried (MgSO$_4$) and concentrated to an oil before being purified by flash chromatography. Elution with a mixture of cyclohexane and ethyl acetate (6:4) provided 1,2,3-tri-O-acetyl-5-O-methyl-β-D-ribofuranose (2.5 g, 62%) as an oil.

9-(2',3'-Di-O-acetyl-5'-methyl-β-D-ribofuranosyl)-2,6-dichloro-9H-purine

5-O-Methyl-1,2,3-tri-O-acetyl-D-ribofuranose (5.0 g, 17 mmol) and 2,6-dichloropurine (3.3 g, 17 mmol) were thoroughly mixed. A catalytic amount of p-toluene sulfuric acid (50 mg) was added and the reaction mixture was heated to 140° C. at which point a homogeneous melt was obtained. The fusion was continued at 140° C. under oil pump vacuum for 0.5 h. The reaction mixture was dissolved in chloroform (200 ml) and washed with aqueous sodium bicarbonate (3×50 ml) and water (2×50 ml). The organic phase was dried (MgSO$_4$), evaporated in vacuo and purified by flash chromatography eluting with a mixture of n-heptane and ethyl acetate (1:1) to provide 9-(2',3'-di-O-acetyl-5'-O-methyl-β-D-ribofuranosyl)-2,6-dichloro-9H-purine (1.0 g, 14%) as an oil which crystallized from diethyl ether. A mixture of α/β-anomers (1.2 g, 17%) was also isolated, with mp 59°–61° C. $^1$H-NMR (400 MHz,CDCL$_3$) δ2.06 (3H, s, —OCOCH$_3$), 3.49 (3H, s, OCH$_3$), 3.67, 3.72 (2H, ABX, H-5'$_a$ and H-5'$_b$), 4.39 (1H, d, H-4'), 5.58 (1H, d, H-3'), 5.75 (1H, t, H-2'), 6.38 (1H, d, H-1'), 8.56 (1H, s, H-8). C$_{15}$H$_{16}$Cl$_2$N$_4$O$_6$ requires C, 43.0; H, 3.9; N, 13.4. Found C, 43.1, H, 3.9, N, 13.2%.

(S)-2',3'-Di-O-acetyl-2-chloro-5'-O-methyl-N-[2-(methylmethoxy)-1-pyrrolidinyl]adenosine.

9-(2',3'-Di-O-acetyl-5'-O-methyl-β-D-ribofuranosyl)-2,6-dichloro-9H-purine (1.3 g, 3.1 mmol), (S)-N-amino-2-(methoxymethyl)pyrrolidine (0.81 g, 6.2 mmol) and triethylamine (0.63 g, 6.2 mmol) were dissolved in dioxan. After stirring for 20 h the reaction mixture was diluted with dichloromethane (150 ml) and washed with water (2×75 ml). The organic phase was dried (MgSO$_4$) and concentrated in vacuo. The resultant residue was purified by flash chromatography eluting with a mixture of dichloromethane and 10% ammonia in ethanol (97:3) to afford (S)-2',3'-di-O-acetyl-2-chloro-5'-O-methyl-N-[2-(methylmethoxy)-1-pyrrolidinyl]adenosine (0.28 g, 18%) as a foam. $^1$H-NMR (400 MHz, CDCl$_3$) δ1.70–2.10 (4H, m, pyrrolidine C—H), 2.05 (3H, s, —OCOCH$_3$), 2.18 (3H, S, —OCOCH$_3$), 2.85 (1H, m, pyrrolidine C—H), 3.10 (1H, br, pyrrolidine C—H), 3.22 (3H, s, —OCH$_3$), 3.35–3.70 (8H, m, H-5'$_a$ and H-5'$_b$, —OCH$_3$, pyrrolidine, —CH$_2$—), 4.32 (1H, s, H-4'), 5.55 (1H, d, H-3'), 5.75 (1H, t, H-3'), 6.32 (1H, d, H-1'), 8.17 (1H, s, H-8). HPLC retention time 15.57 min. (gradient elution over 25 min.; 20–80% acetonitrile/0.1% TFA in water).

The above (S)-2',3'-di-O-acetyl-2-chloro-5'-O-methyl-N-[2-(methylmethoxy)-1-pyrrolidinyl]adenosine (0.26 g, 0.52 mmol) was treated with methanolic ammonia for 1.5 h at room temperature. The crude product was purified by flash chromatography eluting with dichloromethane and 10% ammonia in ethanol (9:1)to give (S)2-chloro-5'-O-methyl-N-(2-methylmethoxy)-1-pyrrolidinyl)adenosine (0.16 g, 72%) as a foam.

$^1$H-NMR (400 MHz, DMSO-d$_6$) δ1.55 (1H, m, pyrrolidine C—H), 1.75 (2H, m, pyrrolidine C—H), 1.97 (1H, m, pyrrolidine C—H), 3.51, 3.59 (1H, ABX, H-5'$_a$ and H-5'$_b$), 4.02 (1H, dd, H-4'), 4.10 (1H, dd, H-3'), 4.52 (1H, dd, H-2'), 5.82 (1H, d, H-1'), 8.32 (1H, s, H-8). HPLC retention time 7.67 min. (gradient elution over 25 min.; 20–80% acetonitrile/0.1% TFA in water). C$_{17}$H$_{25}$ClN$_6$O$_5$.0.5H$_2$O requires C, 46.3; H, 5.8; N, 18.5. Found C, 46.7; H, 6.1; N, 18.6%.

EXAMPLE 21

2-Chloro-5'-deoxy-5'-methylthio-N-(1-piperidinyl)adenosine

The title compound was prepared according to general method C.

2-Chloro-2',3'-O-(1-methylethylidene)-N-(1-piperidinyl) adenosine tosylate salt

2-Chloro-N-(1-piperidinyl)adenosine (1.5 g, 3.9 mmol), 2,2-dimethoxypropane (0.9 g, 8.6 mmol) and 4-toluenesulfonic acid monohydrate (1.6 g, 18.6 mmol) was stirred in acetone (25 ml) for 72 h. Further 2,2-dimethoxypropane (0.9 g, 8.6 mmol) was added. After a further 24 h the tosylate salt of 2-chloro-2',3'-O-(1-methylethylidene)-N-(1-piperidinyl)adenosine (1.78 g, 76%) was collected by filtration, m.p. 169°–170° C., $^1$H-NMR (400 MHz, DMSO-d$_6$) δ1.35 (3H, s, —CH$_3$), 1.46 (2H, br, piperidine C—H), 1.55 (3H, s, —CH$_3$), 1.75 (4H, m, piperidine —CH), 3.10 (4H, br, piperidine C—H), 3.55 (2H, ABX, H-5$_a$' and H-5'$_b$), 4.29 (1H, m, H-4'), 4.95 (1H, dd, H-3'), 5.30 (1H, dd, H-2'), 6.15 (1H, d, H-1'), 8.72 (1H, s, H-8). HPLC retention time 14.87 min. (gradient elution over 30 min.; 20–80% acetonitrile/0.1% TFA in water). C$_{25}$H$_{33}$ClN$_6$O$_7$S requires C, 50.3; H, 5.6; N, 14.1. Found C, 50.7; H, 5.8; N, 13.7%.

2-Chloro-5'-deoxy-5'-methylthio-2',3'-O-(1-methylethylidene)-N-(1-piperidinyl)adenosine 2-Chloro-2',3'-O-(1-methylethylidene)-N-(1-piperidinyl) adenosine tosylate (0.5 g, 0.84 mmol), tributylphosphine (1.7 g, 8.4 mmol) and dimethyldisulfide (0.4 g, 4.20 mmol) were stirred in dry dimethylformamide (5 ml) under nitrogen for 7 days. The reaction mixture was poured into ice (50 ml) and after standing for 1 h was extracted with dichloromethane (3×25 ml). The organic phase was dried (MgSO$_4$) and evaporated in vacuo. The crude product was purified by flash chromatography eluting with a mixture of dichloromethane and 10% ammonia in ethanol (95:5) to give 2-chloro-5'-deoxy-5'-methylthio-2',3'-O-(1-methylethylidene)-N-(1-piperidinyl)adenosine (0.12 g, 31%) as a foam. $^1$H-NMR (400 MHz, CDCl$_3$) δ1.40 (3H, s, —CH$_3$), 1.45 (2H, m, piperidine C—H), 1.65 (3H, s, —CH$_3$), 1.70–1.85 (4H, m, piperidine C—H), 2.15 (3H, s, —SCH$_3$), 2.85 (4H, m, piperidine C—H), 4.02, 4.38 (2H, ABX, H-5'$_a$ and H-5'$_b$), 5.05 (1H, dd, H-4'), 5.38 (1H, dd, H-3'), 6.05 (1H, d, H-2'), 6.50 (1H, br, H-1'), 7.83 (1H, s, H-8).

2-Chloro-5'-deoxy-5'-methylthio-N-(1-piperidinyl)adenosine

2-Chloro-5'-deoxy-5'-methylthio-2',3'-O-(1-methylethylidene)-N-(1-piperidinyl)adenosine (0.10 g, 0.22 mmol) was reacted in a mixture of water (2.5 ml) and ethanol (2.5 ml) containing sulfuric acid (0.1 ml) for 10 h at 60° C. The reaction mixture was diluted with dichloromethane (100 ml) and washed with aqueous sodium bicarbonate (2×25 ml) followed by water (25 ml). The organic phase was dried (MgSO$_4$) and concentrated in vacuo. The crude product was purified by flash chromatography eluting with a mixture of dichloromethane and 10% ammonia in ethanol (95:5) to provide 2-chloro-5'deoxy-5'-methylthio-N-(1-piperidinyl)adenosine (0.75 g, 82%) as a foam, $^1$H-NMR (400 MHz, DMSO-d$_6$) δ1.39 (2H, br, piperidine C—H), 1.62 (4H, m, piperidine C—H), 2.05 (3H, s, —SCH$_3$), 2.75–2.80 (8H, m, H-5'$_a$, H-5'$_b$, piperidine C—H), 4.01 (1H, m, H-4'), 4.10 (1H, m, H-3'), 4.65 (1H, br, H-2'), 6.82 (1H, d, H-1'), 8.39 (1H, s, H-8). HPLC retention time 9.90 min. (gradient elution over 30 min.; 20–80% acetonitrile/0.1% TFA in water, purity 96% at 250 nm).

EXAMPLE 22

2-Chloro-5'-cyano-5'-deoxy-N-(1-piperidinyl)adenosine

The title compound was prepared using general method A starting from 1,2,3-tri-O-acetyl-5-deoxy-5-cyano-D-ribofuranose prepared according to general method B as follows:

Methyl 2,3-O-(1-methylethylidene)-5-O-(4-nitrobenzenesulfonyl)-β-D-ribofuranoside Methyl 2,3-O-(1-methylethylidene)-β-D-ribofuranose (37 g, 180 mmol) and triethylamine (54.6 g, 540 mmol) were dissolved in dry dichloromethane (100 ml). 4-Nitrobenzenesulfonyl chloride (40.0 g, 180 mmol) was added dropwise at 0° C. over 0.5 h. After stirring for 20 h, the reaction mixture was diluted with dichloromethane (1000 ml) and washed with aqueous ammonium chloride (2×250 ml) and water (250 ml). After drying (MgSO$_4$) the organic phase was evaporated to dryness in vacuo. Recrystallization from ethyl acetate gave methyl 2,3-O-(1-methylethylidene)-5-O-(4-nitrobenzenesulfonyl)-β-D-ribofuranoside as a white solid (54.8 g, 85%), m.p. 97°–98° C., $^1$H-NMR (400 MHz, CDCl$_3$) δ1.38 (3H, s, —CH$_3$), 1.45 (3H, s, —CH$_3$), 3.26 (3H, s, —OCH$_3$), 4.13 (2H, ABX, H-5$_a$ and H-5$_b$), 4.32 (1H, t, H-4), 4.53 (1H, d, H-3), 4.61 (1H, d, H-2), 4.95 (1H, s, H-1), 8.12 (2H, d, Ar—H), 8.40 (2H, d, Ar—H).

Methyl 5-cyano-5-deoxy-2,3-O-(1-methylethylidene)-β-D-ribofuranoside.

Methyl 2,3-O-(1-methylethylidene)-5-O-(4-nitrobenzenesulfonyl)-β-D-ribofuranoside (45.3 g, 120 mmol) was added over 1.5 h to a suspension of sodium cyanide (6.8 g, 140 mmol) in dry dimethylformamide (1000 ml). The reaction mixture was heated to 50° C. for 3 h before being poured onto ice (500 ml). This mixture was extracted with dichloromethane (3×500 ml), the combined extracts were dried (MgSO$_4$) and concentrated in vacuo. The residue was distilled under vacuum to give methyl 5-cyano-5-deoxy-2,3-O-(1-methylethylidene)-β-D-ribofuranoside as an oil (6.3 g, 25%), bp 110°–115° C./0.6 mm Hg. $^1$H-NMR (400 MHz, CDCl$_3$) δ1.30 (3H, s, —CH$_3$), 1.48 (3H, s, —CH$_3$), 2.62, 2.70 (2H, ABX, H-5$_a$ and H-5$_b$), 3.40 (3H, s, —OCH$_3$), 4.45 (1H, s, H-4), 4.61 (1H, d, H-3), 4.63 (1H, d, H-2), 5.00 (1H, s, H-1).

Methyl 2,3-di-O-benzoyl-5-cyano-5-deoxy-β-D-ribofuranoside

Methyl 5cyano-5-deoxy-2,3-O-(1-methylethylidene)-β-D-ribofuranoside (18.7 g, 87 mmol) and Amberlyst (H$^+$ form, 84 g) were mixed and heated at reflux for 24 h. The reaction mixture was filtered and evaporated to a residue which was dissolved in dichloromethane (200 ml), which was washed with water (300 ml). The separated water phase was extracted with ethyl acetate (7×200 ml), combined with the earlier organic phase and dried (MgSO$_4$). Evaporation provided the intermediate methyl 5-cyano-5-deoxy-β-D-ribofuranoside (6.85 g) which was dissolved in dichloromethane (200 ml). Benzoyl chloride (24 g, 170 mmol) and triethylamine (34 g, 340 mmol) were introduced and the reaction mixture was stirred for 20 h. at ambient temperature before being washed with 1N hydrochloric acid solution (2×85 ml) and saturated sodium bicarbonate solution. The organic phase was dried (MgSO$_4$) and evaporated to a residue which was purified by flash chromatography on silica gel. Elution with a mixture of heptane and ethyl acetate (39:1), increasing polarity to a 9:1 mixture of these solvents provided methyl 2,3-O-dibenzoyl-5-cyano-5-deoxy-β-D-ribofuranoside (13.01 g, 40%), $^1$H-NMR (400 MHz, CDCl$_3$) δ3.04, 3.20 (2H, ABX, H-5$_a$ and H-5$_b$), 3.43 (3H, s, —OCH$_3$), 4.67 (1H, d, H-4), 5.25 (1H, s, H-1), 5.50–5.57 (2H, m, H-3 and H-4), 7.4–7.95 (10H, 6 m, Ar—H).

1-O-Acetyl-2,3-di-O-benzoyl-5-cyano-5-deoxy-D-ribofuranose

Acetic acid (74.5 ml, 1.3 mol), acetic anhydride (173.8 ml, 1840 mmol) and sulphuric acid (1.7 ml, 32 mmol) were mixed together and methyl 2,3-O-dibenzoyl-5-cyano-5-deoxy-β-D-ribofuranoside (13.01 g, 35 mmol) was added. The reaction mixture was stirred for 20 h at ambient temperature before sodium acetate (37 g, 450 mmol) was introduced. After 30 min. stirring the reaction mixture was filtered, the filter pad was washed with ethyl acetate (100 ml) and the filtrate was evaporated to a residue which was coevaporated with toluene (250 ml). The residue was dissolved in a mixture of ethyl acetate (250 ml) and water (250 ml). The ethyl acetate phase was washed with water (2×100 ml) and saturated brine (50 ml) before being dried (MgSO$_4$) and evaporated. The residue was purified by flash chromatography on silica gel. Elution with a mixture of hexane and ethyl acetate (9:1), increasing polarity to a 4:1 mixture of these solvents provided the title 1-O-acetyl-2,3-di-O-benzoyl-5-cyano-5-deoxy-D-ribofuranose as a solid single isomer (2.85 g, 20%), mp 124°–126° C., $^1$H-NMR (400 MHz, CDCl$_3$) δ2.22 (3H, s, —OCOCH$_3$), 2.92, 3.02 (2H, ABX, H-5$_a$ and H-5$_b$), 4.61 (1H, dt, H-4), 5.70–5.80 (2H, 2m, H-2 and H-3), 6.38 (1H, s, H-1) and a mixture of isomers as a gum (7.5 g, 52%).

9-(2',3'-Di-O-benzoyl-5'-cyano-5'-deoxy-D-ribofuranosyl)-2,6-dichloro-9H-purine

A mixture of 1-O-acetyl-2,3-di-O-benzoyl-5-cyano-5-deoxy-D-ribofuranose (2.8 g, 6.8 mmol) and 2,6-dichloro-9H-purine (1.36 g, 7.2 mmol) were heated at 145° C. for 1.25 h in the presence of a catalytic amount of p-toluenesulphonic acid (0.025 g). The reaction mixture was dissolved in ethyl acetate (100 ml) and washed with aqueous sodium bicarbonate (100 ml) followed by saturated brine (100 ml). The organic phase was dried (MgSO$_4$), and the solid residue was recrystallised from 2-propanol to provide 9-(2',3'-di-O-benzoyl-5'-cyano-5'-deoxy-β-D-ribofuranosyl)-2,6-dichloro-9H-purine (3.3 g, 90%), m.p. 143°–145°

C., $^1$H-NMR (400 MHz, CDCl$_3$) δ3.15, 3.25 (2H, ABX, H-5'$_a$ and H-5'$_b$), 4.74 (1H, dt, H-4'), 5.95 (1H, t, H-3'), 6.12 (1H, t, H-2'), 6.42 (1H, d, H-1'), 7.36–8.05 (10H, 4m, Ar—H), 8.40 (1H, s, H-8).

2',3'-Di-O-benzoyl-2-chloro-5'-cyano-5'-deoxy-N-(1-piperidinyl)adenosine 9-(2',3'-di-O-benzoyl-5'-cyano-5'-deoxy-β-D-ribofuranosyl)-2,6-dichloro-9H-purine (1.75 g, 3.25 mmol), triethylamine (0.9 ml, 6.5 mmol) and 1-aminopiperidine (0.7 ml, 6.5 mmol) were stirred in dioxan (20 ml) for 2 h. The reaction mixture was evaporated and the residue dissolved in dichloromethane (10 ml) and purified by flash chromatography eluting with a mixture of heptane and ethyl acetate (4:1), increasing polarity to a 1:1 mixture of these solvents provided 2',3'-di-O-benzyl-2-chloro-5'-cyano-5'-deoxy-N-(1-piperidinyl)adenosine (1.19 g, 61%) as a foam, $^1$H-NMR (400 MHz, DMSO-d$_6$) δ3.15, 3.31 (2H, ABX, H-5'$_a$ and H-5'$_b$), 4.68 (1H, dd, H-4'), 5.99 (1H, t, H-3'), 6.11 (H, t, H-2'), 6.36 (1H, d, H-1'), 7.36–8.00 (10H, m, Ar—H), 8.03 (1H, s, H-8). HPLC retention time 17.26 min. (gradient elution over 30 min.; 20–80% acetonitrile/0.1% TFA in water).

2-Chloro-5'-cyano-5'-deoxy-N-(1-piperidinyl)adenosine

2',3'-O-Benzoyl-2-chloro-5'-cyano-5'-deoxy-N-(1-piperidinyl)adenosine (1.5 g, 2.5 mmol) was dissolved in methanolic ammonia (30 ml) and stirred at ambient temperature for 3 h. Following evaporation, the crude product was purified by flash chromatography eluting with a mixture of heptane and ethyl acetate, followed by ethyl acetate alone to provide 2-chloro-5'-cyano-5'-deoxy-N-(1-piperidinyl)adenosine as a solid (0.6 g, 61%). Recrystallization from ethyl acetate provided an analytical sample (0.36 g, 37%), m.p. 192°–193° C., $^1$H-NMR (400 MHz, DMSO-d$_6$) δ1.38 (2H, br, piperidine C—H), 1.63 (4H, q, piperidine C—H), 2.81 (4H, br, piperidine C—H), 3.05 (2H, d, H-5'$_a$ and H-5'$_b$), 4.12 (2H, m, H-4' and H-3'), 4.65 (1H, m, H-2'), 5.53, 5.67 (2H, 2d, 2'-and 3'-OH), 5.87 (1H, d, H-1'), 8.37 (1H, s, H-8). HPLC retention time 11.9 min. (gradient elution over 30 min; 25–45% acetonitrile/0.1% ammonium sulfate in water), purity 100% at 250 nm). C$_{16}$H$_{20}$ClN$_7$O$_3$ requires C, 48.8; H, 5.1; N, 24.9. Found C, 48.9; H, 5.3; N, 24.6%.

EXAMPLE 23

2-Chloro-5'-cyano-5'-deoxy-N-(4-phenylthio-1-piperidinyl)adenosine

This compound was prepared by general method A, described in more detail in Example 22. 2',3'-Di-O-benzoyl-2-chloro-5'-cyano-5'-deoxy-N-(4-phenylthio-1-piperidinyl)adenosine [prepared from 1-amino-6-phenylthiopiperidine (Knutsen, L. J. S., Lau, J., Sheardown, M. J., Thomsen, C.; Bioorganic and Medicinal Chemistry Letters, 1993, 3, 2661–2666) and 9-(2',3'-di-O-benzoyl-5'-cyano-5'-deoxy-β-D-ribofuranosyl)-2,6-dichloro-9H-purine as described in Example 24] (1.5 g, 2.5 mmol) in methanol (20 ml) was treated with methanolic ammonia (5 ml). The reaction mixture was stirred at ambient temperature for 0.75 h. Ethyl acetate (5 ml) was added to the residue on evaporation to provide 2-chloro-5'-cyano-5'-deoxy-N-(4-phenylthio-1-piperidinyl)adenosine (0.11 g, 46%) as a solid, m.p. 159°–161° C., $^1$H-NMR (400 MHz, DMSO-d$_6$) δ1.68 (2H, br q, piperidine C—H), 1.98 (2H, m, piperidine C—H), 2.78 (2H, br, piperidine C—H), 3.04 (2H, br d, H-5'$_a$ and H-5'$_b$), 4.11 (2H, m, H-4' and H-3'), 4.63 (1H, m, H-2'), 5.54, 5.68 (2H, 2d, 2'-and 3'-OH), 5.88 (1H, d, H-1'), 7.22–7.45 (5H, 3m, Ar—H), 8.38 (1H, s, H-8), 9.49 (1H, s, N—H). HPLC retention time 20.34 min. (gradient elution over 30 min; 25–45% acetonitrile/0.1% ammonium sulfate in water), purity 96% at 250 nm). C$_{16}$H$_{20}$ClN$_7$O$_3$. 0.7 H$_2$O. 0.1 EtOAc requires C, 51.4; H, 5.1; N, 18.7. Found C, 51.4; H, 4.9; N, 18.3%.

EXAMPLE 24

2-Chloro-5'-deoxy-N-(1-piperidinyl)adenosine

The title compound was prepared using general method A starting from 1-O-acetyl-2,3-di-O-benzoyl-5-deoxy-D-ribofuranose prepared according to general method B as follows: Methyl 2,3-di-O-benzoyl-5'-deoxy-D-ribofuranoside Methyl 5'-deoxy-2,3-O-(1-methylethylidene)-D-ribofuranoside (prepared by reduction of methyl 2,3-O-(1-methylethylidene)-5'-O-(p-toluenesulphonyl)-D-ribofuranoside using lithium aluminium hydride) (4.36 g, 23.2 mmol) was dissolved in methanol (120 ml) and Amberlyst resin (H$^+$ form, 19 g) was introduced. The mixture was stirred at 80° C. for 60 h and filtered. The filter pad was washed with methanol and the filtrate was evaporated to an oily residue. The residue was dissolved in dichloromethane and to this solution was added triethylamine (25.7 g, 185 mmol). Benzoyl chloride (13.08 g, 10.8 ml, 92.8 mmol) was added dropwise over 0.5 h and the reaction mixture was stirred at ambient temperature for 40 h. The reaction mixture was extracted with 0.5M hydrochloric acid solution (2×50 ml) and sodium bicarbonate solution (30 ml) before being dried (MgSO$_4$) and evaporated. The residue was purified by flash chromatography on silica gel eluting with a mixture of heptane and ethyl acetate (4:1), gradually increasing polarity a (1:1) mixture of these solvents, providing the title methyl 2,3-di-O-benzoyl-5'-deoxy-D-ribofuranoside (6.11 g, 74%), $^1$H-NMR (400 MHz, CDCl$_3$) δ1.50 (3H, d, —CHCH$_3$), 3.48 (3H, s, —COCH$_3$), 4.48 (1H, q), 5.11 (1H, s), 5.46 (1H, t), 5.60 (1H, d), 7.25–8.19 (20H, m, Ar—H).

9-(2',3'-Di-O-benzoyl-5'-deoxy-β-D-ribofuranosyl)-2,6-dichloro-9H-purine

1-O-Acetyl-2,3-di-O-benzoyl-5-deoxy-D-ribofuranose [prepared from the above methyl 2,3-di-O-benzoyl-5'-deoxy-D-ribofuranoside by the method described in Lerner, L. Nucleic Acid Chemistry: Improved and New Synthetic Procedures, Methods and Techniques, Part Four. Townsend, L. B. and Tipson, R. S., Eds.; John Wiley and Sons, New York, 1991, pp 274–280] (1.02 g, 2.65 mmol) and 2,6-dichloro-9H-purine (0.48 g, 2.53 mmol) were mixed thoroughly and heated at 145° C. under oilpump vacuum for 2 h. The cooled reaction mixture was dissolved in dichloromethane (25 ml), evaporated, and coevaporated with toluene (2 ×50 ml). Purification of the residue by flash chromatography provided the title 9-(2',3'-di-O-benzoyl-5'-deoxy-β-D-ribofuranosyl)-2,6-dichloro-9H-purine (0.90 g, 58%) as a foam, $^1$H-NMR (400 MHz, DMSO-d$_6$) δ1.67 (3H, d, —CHCH$_3$), 4.64 (1H, dt, H-4'), 5.72 (1H, t, H-3'), 6.12 (1H t, H-2'), 6.35 (1H, d, H-1'), 7.31–8.05 (10H, m, Ar—H), 8.31 (1H, s, H-8).

2',3'-Di-O-benzoyl-2-chloro-5'-deoxy-N-(1-piperidinyl)adenosine 9-(2',3'-Di-O-benzoyl-5'-deoxy-β-D-ribofuranosyl)-2,6-dichloro-9H-purine (0.46 g, 0.75 mmol) was dissolved in dioxan (10 ml). 1-Aminopiperidine (0.06 ml, 0.90 mmol) and triethylamine (0.16 ml, 1.13 mmol) were added and the reaction mixture was stirred at ambient temperature for 18 h before being evaporated.

The residue was treated with water (50 ml) and ethyl acetate (100 ml). The organic phase was separated and washed with water (2×50 ml). The combined extracts were dried (MgSO$_4$) and evaporated. The residue was purified by flash chromatography on silica gel eluting with a mixture of heptane and ethyl acetate (1:1) to provide the title 2,3-di-O-benzoyl-2-chloro-5'-deoxy-N-(1-piperidinyl)adenosine (0.30 g, 69%) as a foam, $^1$H-NMR (400 MHz, CDCl$_3$) 1.48 (2H, br, piperidine C—H), 1.80 (2H, m, piperidine C—H), 2.87 (2H, br, piperidine C—H), 4.57 (1H, dt, H-4'), 5.71 (1H, t, H-3'), 6.07 (1H, t, H-2'), 6.33 (1H, d, H-1'), 7.28–8.00 (11H, m, Ar—H and H-8).

2-Chloro-5'-deoxy-N-(1-piperidinyl)adenosine 2,3-Di-O-benzoyl-2-chloro-5'-deoxy-N-(1-piperidinyl)adenosine (0.30 g, 0.81 mmol) was dissolved in methanol (10 ml) and methanolic ammonia (5 ml) was introduced. The reaction mixture was stirred at ambient temperature for 18 h. and evaporated. The residue was purified by flash chromatography eluting with a mixture of dichloromethane and 10% ammonia in ethanol (95:5) to provide the title 2-chloro-5'-deoxy-N-(1-piperidinyl)adenosine (0.13 g, 43%) as a foam, $^1$H-NMR (400 MHz, DMSO-d$_6$) δ1.21–1.43 (5H, m, piperidine C—H and CHC$\underline{H}_3$), 1.63 (4H, br q, piperidine C—H), 2.82 (4H, br m, piperidine C—H), 5.79 (1H, d, H-1'), 8.37 (1H, s, H-8), 9.32 (1H, s, N—H). HPLC retention time 6.82 min. (gradient elution over 30 min; 25–45% acetonitrile/0.1% ammonium sulfate in water).

EXAMPLE 25

2-Chloro-5'-deoxy-5'-methylene-N-(1-piperidinyl)adenosine

Methyl 5-deoxy-5'-methylene-2,3-O-(1-methylethylidene)-D-ribofuranoside Triphenylmethylphosphonium bromide (26.79 g, 75 mmol) was suspended in THF (200 ml) and n-butyllithium (1.7M in hexanes) (42 ml, 71.2 mmol) was introduced. After stirring for 2 h, methyl 5-deoxy-5-oxo-2,3-O-(1-methylethylidene)-D-ribofuranoside (prepared by oxidation of 1-O-methyl-2,3-O-(1-methylethylidene)-D-ribofuranoside using the method described in Ranganathan, R. S., Jones, G. H. and Moffatt, J. G., Journal of Organic Chemistry, 1974, 39(3), 290–298) (5.06 g, 25 mmol) in THF (50 ml) was added dropwise. The reaction mixture was heated for 2 h at 50° C. and cooled. A mixture of water (10 mL) and THF (90 ml) were added carefully under a stream of nitrogen. Diethyl ether (250 ml) and water (250ml) were introduced. The aqueous phase was washed with diethyl ether (250 ml) and the combined organic extracts were washed with saturated brine (150 ml) and dried (MgSO$_4$). The residue on evaporation was purified by flash chromatography eluting with a mixture of cyclohexane and ethyl acetate (19:1 ), increasing polarity to a mixture of heptane and ethyl acetate (9:1) provided the desired methyl 5-deoxy-2,3-O-(1-methylethylidene)-5-methylene-D-ribofuranoside (3.6 g, 72%) as a gum, $^1$H-NMR (400 MHz, CDCl$_3$) δ1.32, 1.50 (6H, 2 s, C(CH$_3$)$_2$), 3.36 (3H, s, —COCH$_3$), 4.64 (1H, s), 4.65 (1H, d), 5.00 (1H, s), 5.15 (1H, d), 5.26 (1H, d), 5.83–5.92 (1H, m).

Methyl 2,3-di-O-benzoyl-5-deoxy-5-methylene-D-ribofuranoside

Methyl 5-deoxy-2,3-O-(1-methylethylidene)-5-methylene-D-ribofuranoside (5.65 g, 28.2 mmol) was dissolved in methanol (250 ml) and Amberlyst resin (H$^+$ form, 30 g) was introduced. The mixture was stirred at ambient temperature for 40 h and was filtered. The filter pad was washed with methanol and the filtrate was evaporated to an oily residue. The residue was dissolved in dichloromethane and to this solution was added benzoyl chloride (8.47 g, 7.0 ml, 60 mmol) and triethylamine (6.49 g, 8.94 ml, 66 mmol) and the reaction mixture was stirred at ambient temperature for 18 h. The reaction mixture was extracted with 0.5M hydrochloric acid solution (2×100 ml) and water (100 ml) before being dried (MgSO$_4$) and evaporated. The residue was purified by flash chromatography on silica gel eluting with a mixture of heptane and ethyl acetate (29:1), gradually increasing polarity to a (4:1) mixture of these solvents, providing the title methyl 2,3-di-O-benzoyl-5-deoxy-5-methylene-D-ribofuranoside (1.66 g, 26%), $^1$H-NMR (400 MHz, CDCl$_3$) δ3.50 (3H, s, —COCH$_3$), 4.75–4.82 (1H, m), 5.16 (1H, s), 5.30 (1H, d), 5.45 (1H, d), 5.61 (1H, d), 5.94–6.09 (1H, m).

9-(2',3'-Di-O-benzoyl-5'-deoxy-5'-methylene-β-D-ribofuranosyl)-2,6-dichloro-9H-purine 1-O-Acetyl-2,3-di-O-benzoyl-5-deoxy-5-methylene-D-ribofuranose [prepared from the above methyl 2,3-di-O-benzoyl-5-deoxy-(1-methylethylidene)-5-methylene-D-ribofuranoside by the method described in Lerner, L. Nucleic Acid Chemistry: Improved and New Synthetic Procedures, Methods and Techniques, Part Four. Townsend, L. B. and Tipson, R. S., Eds.; John Wiley and Sons, New York, 1991, pp 274–280] (4.2 g, 10.6 mmol) and 2,6-dichloro-9H-purine (2.0 g, 10.6 mmol) were suspended in dichloromethane (25 ml) and evaporated to a residue which was heated at 150° C. under oilpump vacuum for 1.5 h. The cooled reaction mixture was dissolved in dichloromethane (25 ml), evaporated, and coevaporated with toluene (2×50 ml). Purification of the residue by flash chromatography eluting with a mixture of heptane and ethyl acetate (9:1), increasing polarity to a mixture of heptane and ethyl acetate (4:1) provided the title 2,6-dichloro-9-(5'-deoxy-2',3'-di-O-benzoyl-5'-methylene-β-D-ribofuranosyl)-9H-purine (3.98 g, 71%) as a foam, $^1$H-NMR (400 MHz, DMSO-d$_6$) δ4.98 (1H, d), 5.48 (1H, d), 5.58 (1H, d), 5.91 (1H, t), 6.16 (1H, t, H-2'), 6.22 (1H, m), 6.44 (1H, d, H-1'), 7.34–8.08 (10H, m, Ar—H), 8.34 (1H, s, H-8). HPLC retention time 15.51 min. (gradient elution over 30 min.; 20–80% acetonitrile/0.1% TFA in water).

2',3'-Di-O-benzoyl-2-chloro-5'-deoxy-5'-methylene-N-(1-piperidinyl)adenosine 2,6-Dichloro-9-(5'-deoxy-2',3'-di-O-benzoyl-5'-methylene-β-D-ribofuranosyl)-9H-purine (0.3 g, 0.57 mmol) was dissolved in dioxan (20 ml). 1-Aminopiperidine (0.066 g, 0.63 mmol) and triethylamine (0.087 g, 0.12 ml, 0.86 mmol) were added and the reaction mixture was stirred at ambient temperature for 40 h and evaporated. The residue was purified by flash chromatography on silica gel eluting with a mixture of heptane and ethyl acetate (4:1), gradually increasing polarity to a (1:1) mixture of these solvents, to afford the title 2,3-di-O-benzoyl-2-chloro-5'-deoxy-5'-methylene-N-(1-piperidinyl)adenosine (0.28 g, 83%), $^1$H-NMR (400 MHz, CDCl$_3$) δ4.93 (1H, dt), 5.43 (1H, dd), 5.56 (1H, d), 5.89 (1H, t), 6.10 (1H, t, H-2'), 6.21 (1H, m), 6.42 (1H, d, H-1'), 7.33–8.05 (10H, m, Ar—H).

2-Chloro-5'-deoxy-5'-methylene-N-(1-piperidinyl)adenosine 2,3-Di-O-benzoyl-2-chloro-5'-deoxy-5'-methylene-N-(1-piperidinyl)adenosine (0.28 g, 0.47 mmol) was dissolved in methanolic ammonia (10 ml) and stirred at ambient temperature for 18 h. The reaction mixture was evaporated and purified by flash chromatography eluting with a mixture of dichloromethane and 10% ammonia in ethanol (95:5) to provide the title 2-chloro-5'-deoxy-5'-methylene-N-(1-piperidinyl)adenosine (0.081 g, 45%) as a foam, $^1$H-NMR (400

MHz, DMSO-d$_6$) δ1.30–1.45 (2H, br m, piperidine C—H), 1.62 (4H, br q, piperidine C—H), 2.84 (4H, br, piperidine C—H), 4.07 (1H, dt, H-3'), 4.32 (1H, q, H-2'), 4.58 (1H, m, H-4'), 5.20 (1H, dd, C=C—H), 5.30 (1H, d, C=C—H), 5.40, 5.56 (2H, 2d, 2'-and 3'-OH), 5.86 (1H, d, H-1'), 6.07 (1H, m, C=C—H), 8.36 (1H, s, H-8), 9.34 (1H, s, N—H). HPLC retention time 9.35 min. (gradient elution over 30 min; 25–45% acetonitrile/0.1% ammonium sulfate in water), purity 99.5% at 250 nm).

EXAMPLE 26

2-Chloro-5'-deoxy-5'-methylene-N-(4-phenylthio-1-piperidinyl)adenosine

2',3'-Di-O-benzoyl-2-chloro-5'-deoxy-5'-methylene-N-(4-phenylthio-1-piperidinyl)adenosine, prepared as described in Example 25 from 2,6-dichloro-9-(5'-deoxy-2',3'-di-O-benzoyl-5'-methylene-β-D-ribofuranosyl)-9H-purine (1.0 g, 1.9 mmol) and 1-amino-4-phenylthiopiperidine (0.44 g, 2.1 mmol), was dissolved in methanol (20 ml) and sat. methanolic ammonia (2.5 ml) was introduced. The reaction mixture was stirred at ambient temperature for 18 h, evaporated and purified by flash chromatography eluting with a mixture of dichloromethane and ethanol (50:1) to provide the title 2-chloro-5'-deoxy-5'-methylene-N-(4-phenylthio-1-piperidinyl)adenosine (0.27 g, 29%) as a foam, $^1$H-NMR (400 MHz, DMSO-d$_6$) δ1.70 (2H, br q, piperidine C—H), 1.99 (2H, br d, piperidine C—H), 2.77 (2H, br m, piperidine C—H), 3.06 (2H, br m, piperidine C—H), 4.07 (1H, q, H-3'), 4.32 (1H, dt, H-2'), 4.58 (1H, m, H-4'), 5.20 (1H, dd, C=C—H), 5.29 (1H, d, C=C—H), 5.39, 5.56 (2H, 2d, 2'-and 3'-OH), 5.86 (1H, d, H-1'), 6.07 (1H, m, C=C—H), 7.23–7.45 (5H, 3 m, Ar—H), 8.36 (1H, s, H-8), 9.34 (1H, s, N—H). HPLC retention time 13.46 min. (gradient elution over 30 min; 25–45% acetonitrile/0.1% ammonium sulfate in water), purity 100% at 250 nm).

EXAMPLE 27

2-Chloro-5'-deoxy-N-methoxy-5'-methyleneadenosine

2',3'-Di-O-benzoyl-2-chloro-5'-deoxy-N-methoxy-5'-methyleneadenosine (0.2 g, 0.4 mmol), prepared by the method described in Example 25 from 2,6-dichloro-9-(2',3'-di-O-benzoyl-5'-methylene-β-D-ribofuranosyl)-9H-purine (0.5 g, 2.0 mmol) and O-methylhydroxlamine hydrochloride (0.167 g, 2.0 mmol), was treated with methanolic ammonia (10 ml) and stirred at ambient temperature for 18 h. The reaction mixture was evaporated and purified by flash chromatography eluting with a mixture of dichloromethane and 10% ammonia in ethanol (19:1) to provide the title 2-chloro-5'-deoxy-N-methoxy-5'-methyleneadenosine (0.03 g, 9%) as a foam, $^1$H-NMR (400 MHz, DMSO-d$_6$) δ3.79 (3H, s, —CH$_3$), 4.08 (1H, q, H-3'), 4.33 (1H, dt, H-2'), 4.61 (1H, m, H-4'), 5.20 (1H, dd, C=C—H), 5.31 (1H, d, C=C—H), 5.42, 5.59 (2H, 2d, 2'-and 3'-OH), 5.89 (1H, d, H-1'), 6.08 (1H, m, C=C—H), 8.44 (1H, s, H-8), 11.58 (1H, s, N—H). HPLC retention time 7.09 min. (gradient elution over 30 min; 25–45 % acetonitrile/0.1% ammonium sulfate in water), purity 98.6% at 250 nm).

EXAMPLE 28

2-Chloro-5'-deoxy-5'-methylene-N-cyclopentyladenosine 2,3-Di-O-benzoyl-2-chloro-5'-deoxy-5'-methylene-N-cyclopentyladenosine (prepared by reaction of 2,6-dichloro-9-(5'-deoxy-2',3'-di-O-benzoyl-5'-methylene-β-D-ribofurano- syl)-9H-purine with cyclopentylamine) (0.30 g, 0.52 mmol) was dissolved in methanolic ammonia (10 ml) and stirred at ambient temperature for 18 h. The reaction mixture was evaporated and purified by flash chromatography eluting with a mixture of dichloromethane and 10% ammonia in ethanol (39:1) to provide the title 2-chloro-5'-deoxy-5'-methylene-N-cyclopentyladenosine (0.051 g, 27%) as a foam, $^1$H-NMR (400 MHz, DMSO-d$_6$) δ1.48–2.04 (8H, 3 br m, cyclopentyl C—H), 4.08 (1H, q, H-3'), 4.32 (1H, dt, H-2'), 4.42 (1H, m, —HN—C—H), 4.59 (1H, m, H-4'), 5.19 (1H, dd, C=C—H), 5.30 (1H, d, C=C—H), 5.40, 5.55 (2H, 2d, 2'-and 3'-OH), 5.85 (1H, d, H-1'), 6.08 (1H, m, C=C—H), 8.34 (1H, s & br s, H-8 and N—H).

EXAMPLE 29

5'-Deoxy-2,5'-dichloro-N-(4-phenylthiocyclohexyl)adenosine

This compound was prepared by general method C, described in more detail in Example 2. 2-Chloro-N-(4-phenylthiocyclohexyl)adenosine (prepared from 4-hydroxycyclohexlamine by the general methods laid out in Knutsen, L. J. S., Lau, J., Sheardown, M. J., Thomsen, C.; Bioorganic and Medicinal Chemistry Letters, 1993, 3, 2661–2666) (0.2 g, 0.44 mmol) was subjected to the reaction conditions described above, and the residue on evaporation was purified by flash chromatography on silica gel eluting with a mixture of heptane and ethyl acetate (4:1), gradually increasing polarity to a (19:1) mixture of ethyl acetate and methanol to afford the title 5'-deoxy-2,5'-dichloro-N-(4-phenylthiocyclohexyl)adenosine (0.08 g, 38%), $^1$H-NMR (400 MHz, CDCl$_3$) δ1.20–1.30 (2H, t, cyclohexyl C—H), 1.80–2.05 (6H, br m, cyclohexyl C—H), 3.75–3.84 (2H, m, H-5'$_a$ and H-5'$_b$), 5.96 (1H, d, H-1'), 7.19–7.33 (3H, m, Ar—H), 7.41 (2H, d, Ar—H), 7.99 (1H, s, H-8), 8.29 (1H, s, N—H). HPLC retention time 9.1 min. (gradient elution over 30 min.; 20–80% acetonitrile/0.1% TFA in water, 100% purity at 250 nm).

We claim:
1. A compound of formula (I) or a pharmaceutically acceptable salt thereof

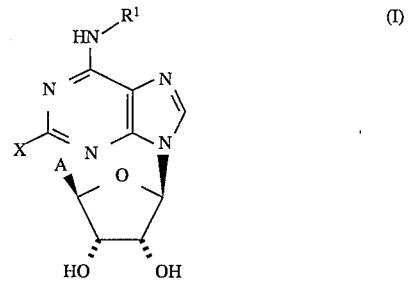

wherein
X is halogen, amino, perhalomethyl, cyano, C$_{1-6}$-alkoxy, C$_{1-6}$-alkylthio or C$_{1-6}$-alkylamino;
A is methyl, halomethyl, cyanomethyl, aminomethyl, vinyl, methylthiomethyl or methoxymethyl; and
R$^1$ is selected from the group consisting of
(i) a ring of formula (a)

wherein Q is nitrogen, n is 2 and the ring of formula (a) is unsubstituted or substituted with one or two $C_{1-6}$-alkyl groups, $C_{2-6}$-alkenyl, $C_{2-6}$-alkynyl, phenoxy, phenylsulphonyl, phenylsulphinyl, phenylthio, hydroxy, phenyl, $C_{1-6}$-alkoxy, $C_{1-6}$-alkoxy-$C_{1-6}$-alkyl, or phenylthioalkyl, (ii) a ring of formula (b)

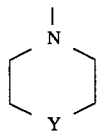

(b)

wherein Y is O, S or NZ, wherein Z is H, $C_{1-6}$-alkyl or phenyl, and wherein the ring of formula (b) is unsubstituted or substituted with $C_{1-6}$-alkyl, $C_{2-6}$-alkenyl, $C_{2-6}$-alkynyl, phenoxy, phenyl, $C_{1-6}$-alkoxy or $C_{1-6}$-alkoxy-$C_{1-6}$-alkyl, and (iii) —$NR^2R^3$ or —$Y^2R^4$, wherein $Y^2$ is oxygen or sulphur; $R^2$ is $C_{1-6}$-alkyl; $R^3$ is phenyl or $C_{1-6}$-alkyl which is unsubstituted or substituted by phenyl or phenoxy; and $R^4$ is $C_{1-6}$-alkyl or $C_{3-8}$-cycloalkyl, each of which is unsubstituted or substituted by phenyl or phenoxy.

2. A compound of claim 1 wherein

X is halogen, amino, $C_{1-6}$-alkylthio or $C_{1-6}$-alkylamino;

A is methyl, halomethyl, cyanomethyl, vinyl, methylthiomethyl or methoxymethyl; and $R^1$ is a ring of formula (a)

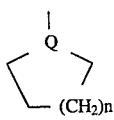

(a)

wherein Q is nitrogen, n is 2 and the ring of formula (a) is unsubstituted or substituted with one or two $C_{1-6}$-alkyl groups, $C_{2-6}$-alkenyl, $C_{2-6}$-alkynyl, phenoxy, phenylsulphonyl, phenylsulphinyl, phenylthio, hydroxy, phenyl, $C_{1-6}$-alkoxy or $C_{1-6}$-alkoxy-$C_{1-6}$-alkyl, phenylthioalkyl.

3. A compound of claim 1, wherein

X is halogen, amino, $C_{1-6}$-alkylthio or $C_{1-6}$-alkylamino;

A is methyl, halomethyl, cyanomethyl, vinyl, methylthiomethyl or methoxymethyl; and $R^1$ is a ring of formula (b)

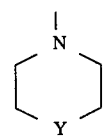

(b)

wherein Y is O, S or NZ, wherein Z is H, $C_{1-6}$-alkyl or phenyl, and wherein the ring of formula (b) is unsubstituted or substituted with $C_{1-6}$-alkyl, $C_{2-6}$-alkenyl, $C_{1-6}$-alkynyl, phenoxy, phenyl, $C_{1-6}$-alkoxy or $C_{1-6}$-alkoxy-$C_{1-6}$-alkyl.

4. A compound of claim 1, wherein

X is halogen, amino, $C_{1-6}$-alkylthio or $C_{1-6}$-alkylamino;

A is methyl, halomethyl, cyanomethyl, vinyl, methylthiomethyl or methoxymethyl; and $R^1$ is —$NR^2R^3$ or —$Y^2R^4$, wherein $Y^2$ is oxygen or sulphur, $R^2$ is $C_{1-6}$-alkyl; $R^3$ is phenyl or $C_{1-6}$-alkyl which is unsubstituted or substituted by phenyl or phenoxy; and $R^4$ is $C_{1-6}$-alkyl or $C_{3-8}$-cycloalkyl, which is unsubstituted or substituted by phenyl or phenoxy.

5. A compound of claim 1 which is 2,5'-Dichloro-5'-deoxy-N-(1-piperidinyl)adenosine;

2,5'-Dichloro-5'-deoxy-N-(4-phenoxy-1-piperidinyl)adenosine;

2,5'-Dichloro-5'-deoxy-N-(3-methoxy-1-piperidinyl)adenosine;

2,5'-Dichloro-5'-deoxy-N-(4-phenylthio-1-piperidinyl)adenosine;

2,5'-Dichloro-5'-deoxy-N-(3-phenylthio-1-piperidinyl)adenosine;

2,5'-Dichloro-5'-deoxy-N-(4-phenylsulphinyl-1-piperidinyl)adenosine;

2,5'-Dichloro-5'-deoxy-N-(4-phenylsulphonyl-1-piperidinyl)adenosine;

2,5'-Dichloro-5'-deoxy-N-(4-phenyl-1-piperidinyl)adenosine;

2-Bromo-5'-chloro-5'-deoxy-N-(1-piperidinyl)adenosine;

2-Amino-5'-chloro-5'-deoxy-N-(4-phenylthio-1-piperidinyl)adenosine;

5'-Chloro-5'-deoxy-2-methylthio-N-(1-piperidinyl)adenosine;

5'-Bromo-2-chloro-5'-deoxy-N-(1-piperidinyl)adenosine;

2-Chloro-5'-deoxy-5'-fluoro-N-(1-piperidinyl)adenosine;

2-Chloro-5'-deoxy-5'-methylthio-N-(1-piperidinyl)adenosine;

2-Chloro-5'-cyano-5'-deoxy-N-(1-piperidinyl)adenosine;

2-Chloro-5'-cyano-5'-deoxy-N-(4-phenylthio-1-piperidinyl)adenosine;

2-Chloro-5'-deoxy-N-(1-piperidinyl)adenosine;

2-Chloro-5'-deoxy-5'-methylene-N-(1-piperidinyl)adenosine;

2-Chloro-5'-deoxy-5'-methylene-N-(4-phenylthio-1-piperidinyl)adenosine; or a pharmaceutically acceptable salt thereof.

6. A compound of claim 1 which is 2,5'-Dichloro-5'-deoxy-N-(1-morpholinyl)adenosine; or pharmaceutically acceptable salt thereof.

7. A compound of claim 1 which is 2,5'-Dichloro-5'-deoxy-N-(dimethylamino)adenosine;

2,5'-Dichloro-5'-deoxy-N-methoxyadenosine;

N-Cyclopentoxy-2,5'-dichloro-5'-deoxy-adenosine;

2-Chloro-5'-deoxy-5'-fluoro-N-benzyloxyadenosine; or a pharmaceutically acceptable salt thereof.

8. A compound of claim 1 which is

2-Chloro-5'-deoxy-N-methoxy-5'-methyleneadenosine; or a pharmaceutically acceptable salt thereof.

9. A pharmaceutical composition comprising as active component a compound according to claim 1 and a pharmaceutically acceptable carrier.

10. A pharmaceutical composition according to claim 9 in the form of an oral dosage unit containing about 1–200 mg of the active compound.

11. A method of treating myocardial ischemia in a person in need thereof, comprising administering an effective amount of a compound according to claim 1.

12. A method of treating myocardial ischemia in a subject in need thereof, comprising administering a pharmaceutical composition according to claim 9.

13. A method of treating cerebral ischemia in a person in need thereof, comprising administering an effective amount of a compound according to claim 1.

14. A method of treating cerebral ischemia in a subject in need thereof, comprising administering a pharmaceutical composition according to claim 9.

* * * * *